United States Patent
Stein

(10) Patent No.: US 9,555,251 B2
(45) Date of Patent: Jan. 31, 2017

(54) SYSTEMS AND METHODS FOR ADJUSTING A PACING RATE BASED ON CARDIAC PRESSURE

(75) Inventor: Paul M. Stein, Oxnard, CA (US)

(73) Assignee: Pacesetter, Inc., Sylmar, CA (US)

(*) Notice: Subject to any disclaimer, the term of this patent is extended or adjusted under 35 U.S.C. 154(b) by 2119 days.

(21) Appl. No.: 12/349,449

(22) Filed: Jan. 6, 2009

(65) Prior Publication Data

US 2010/0174336 A1 Jul. 8, 2010

(51) Int. Cl.
*A61N 1/365* (2006.01)

(52) U.S. Cl.
CPC .................. *A61N 1/36564* (2013.01)

(58) Field of Classification Search
USPC ......... 607/1–2, 9, 15, 17–18, 23, 30, 32, 60, 62,607/115–116, 119, 122; 600/301, 485, 486
See application file for complete search history.

(56) References Cited

U.S. PATENT DOCUMENTS

| 5,129,394 A * | 7/1992 | Mehra .............................. 607/23 |
| 2006/0149324 A1 | 7/2006 | Mann et al. |
| 2006/0149330 A1 | 7/2006 | Mann et al. |
| 2006/0149331 A1 | 7/2006 | Mann et al. |

FOREIGN PATENT DOCUMENTS

WO    2005062823 A2    7/2005

* cited by examiner

*Primary Examiner* — Deborah Malamud

(57) ABSTRACT

An implantable medical device includes a pressure input, an excitation source, a detector module, and a processor. The pressure input is configured to be joined to a pressure sensor located proximate to a cardiac chamber of the heart. The pressure input receives pressure measurements representative of a pressure in the cardiac chamber. The excitation source is configured to deliver stimulation pulses to the heart. The detector module communicates with the pressure sensor to receive and compare the pressure measurements to a pressure threshold. The processor instructs the excitation source to deliver the stimulation pulses at a pressure-based rate based on the comparison of the pressure measurements to the pressure threshold.

18 Claims, 10 Drawing Sheets

SYSTEMS AND METHODS FOR ADJUSTING A PACING RATE BASED ON CARDIAC PRESSURE

FIELD OF THE INVENTION

Embodiments of the present invention pertain generally to implantable and external medical devices and more particularly pertain to methods and systems that monitor cardiac chamber pressure.

BACKGROUND OF THE INVENTION

Atrial fibrillation is a cardiac arrhythmia that results in an irregular heartbeat. With atrial fibrillation, the normal electric impulses generated by the myocardium are overwhelmed by other electrical impulses in the heart. Atrial fibrillation includes the conduction of irregular impulses to the ventricles of the myocardium, which in turn generate the cardiac cycles of the heart and may result in disruption of the normal sinus rhythm of the heart. When left untreated, atrial fibrillation may become a chronic condition and lead to an increase in the risk of death.

Implantable medical devices ("IMDs") may be implanted in a patient to monitor, among other things, electrical activity of a heart and to deliver appropriate electrical and/or drug therapy to treat atrial fibrillation, as required. IMDs include, for example, pacemakers, cardioverters, defibrillators, implantable cardioverter defibrillators ("ICD"), cardiac resynchronization therapy ("CRT") devices, and the like. The electrical therapy produced by an IMD may include, for example, pacing pulses, cardioverting pulses, and/or defibrillator pulses to reverse arrhythmias (e.g., atrial and/or ventricular fibrillation, tachycardias, and bradycardias) or to stimulate the contraction of cardiac tissue (e.g., cardiac pacing) to return the heart to its normal sinus rhythm.

Known IMDs do not address some potential causes of atrial fibrillation. For example, one potential cause is atrial volume overload. Atrial volume overload represents the build up of fluid pressure in the left and/or right atria. As the pressure in the left and/or right atria increases, at least a portion of the myocardium stretches. Stretching of the myocardium in or near the atria may result in morphological and electrophysiological changes, which in turn may lead to the generation and maintenance of atrial fibrillation.

The body has a normal physiological mechanism to prevent atrial volume overload. This mechanism is referred to as the Bainbridge reflex, whereby an abnormally large amount of blood in the atria is sensed by stretch receptors in the atria. The stretch receptors signal the medulla of the brain to induce a reflex increase in the heart rate. Increasing the heart rate may increase the flow of fluid out of the atria in the heart and consequently reduce atrial pressure in the atria. As the atrial pressure is reduced, the atrial volume overload in the heart may be reduced. If the atrial volume overload can be reduced or prevented, especially in the early stages of pressure build-up in the atria, then the stretch-induced atrial fibrillation may be reduced or prevented. Moreover, even in patients with a long term history of coronary disease resulting in chronic atrial fibrillation, reducing atrial volume overload may result in the stretched myocardium in or near the atria reducing in size and thereby remodel. Atrial remodeling may, in turn, reduce the atrial fibrillation burden on the patient.

The potential exists that the Bainbridge reflex may either completely or partially fail in some patients, thus leaving these patients more susceptible to atrial volume overload and, consequently, atrial fibrillation. A need exists for a system and method that reduces atrial volume overload and thereby reduces the amount of stretch in the myocardium and consequently reduces or prevents the onset of stretch-induced atrial fibrillation.

BRIEF SUMMARY OF THE INVENTION

In one embodiment, a medical device includes a pressure input, an excitation source, a detector module, and a processor. The pressure input is configured to be joined to a pressure sensor located proximate to a cardiac chamber. The pressure input receives pressure measurements representative of a pressure in the cardiac chamber. The excitation source is configured to deliver stimulation pulses to a myocardium. The detector module communicates with the pressure sensor to receive and compare the pressure measurements to a pressure threshold. The processor instructs the excitation source to deliver the stimulation pulses at a pressure-based rate based on the comparison of the pressure measurements to the pressure threshold. Optionally, the pressure sensor is located in at least one of the superior vena cava, a pulmonary artery, a pulmonary vein, and a chamber of the heart (collectively referred to as a cardiac chamber). The processor may instruct the excitation source to change a rate at which the stimulation pulses are delivered from an initial pacing rate to the pressure-based rate.

In another embodiment, a method for reducing a pressure in a cardiac chamber is provided. The method includes obtaining pressure measurements representative of the pressure in the cardiac chamber and comparing the pressure measurements to a pressure threshold. The method further includes delivering stimulation pulses to the myocardium at a pressure-based rate based on the comparing of the pressure measurement to the pressure threshold. Optionally, the method includes accelerating the pressure-based rate from an initial pacing rate to a target rate at a predetermined acceleration rate.

In another embodiment, a computer readable storage medium for use in a medical device having a memory, a programmable microcontroller and an excitation source configured to deliver stimulation pulses to the myocardium is provided. The computer readable storage medium includes instructions to direct the microcontroller to obtain pressure measurements from a pressure sensor and compare the pressure measurements to a pressure threshold. The pressure measurements are representative of a pressure in the cardiac chamber. The instructions also direct the microcontroller to instruct the excitation source to deliver the stimulation pulses at a pressure-based rate based on the comparison of the pressure measurements to the pressure threshold.

BRIEF DESCRIPTION OF THE DRAWINGS

The drawings illustrate generally, by way of example, but not by way of limitation, various embodiments discussed in the present document.

DETAILED DESCRIPTION OF THE INVENTION

In the following detailed description, reference is made to the accompanying drawings which form a part hereof, and in which are shown by way of illustration specific embodiments in which the present invention may be practiced. These embodiments, which are also referred to herein as "examples," are described in sufficient detail to enable those skilled in the art to practice the invention. It is to be understood that the embodiments may be combined or that other embodiments may be utilized, and that structural, logical, and electrical variations may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

In accordance with certain embodiments, methods and systems are provided that are able to monitor cardiac chamber pressure and trigger, adjust and/or terminate a pacing therapy in response thereto to reduce the cardiac chamber pressure. In one embodiment, the systems and methods described herein provide for the sensing, integrating, and pacing components of the Bainbridge reflex of a patient exhibiting stable myocardial behavior. For example, an IMD 100 and process 200 described below may emulate the Bainbridge reflex in a patient by monitoring physiological parameters such as the cardiac chamber pressure in real-time, and correspondingly adjust the heart rate of the patient in response to the physiological parameters. The monitoring of the cardiac chamber pressure and the application of a pressure-reduction therapy may aid in reducing atrial overload, for example, and thereby reduce the risk of atrial fibrillation. Moreover, by reducing or preventing atrial volume overload over an extended period of time, the cellular components of the atria may remodel. For example, atria that have become stretched due to atrial volume overload may decrease in size over time, thereby reducing the morphological and electrophysiological substrate of atrial fibrillation.

Figure 1:
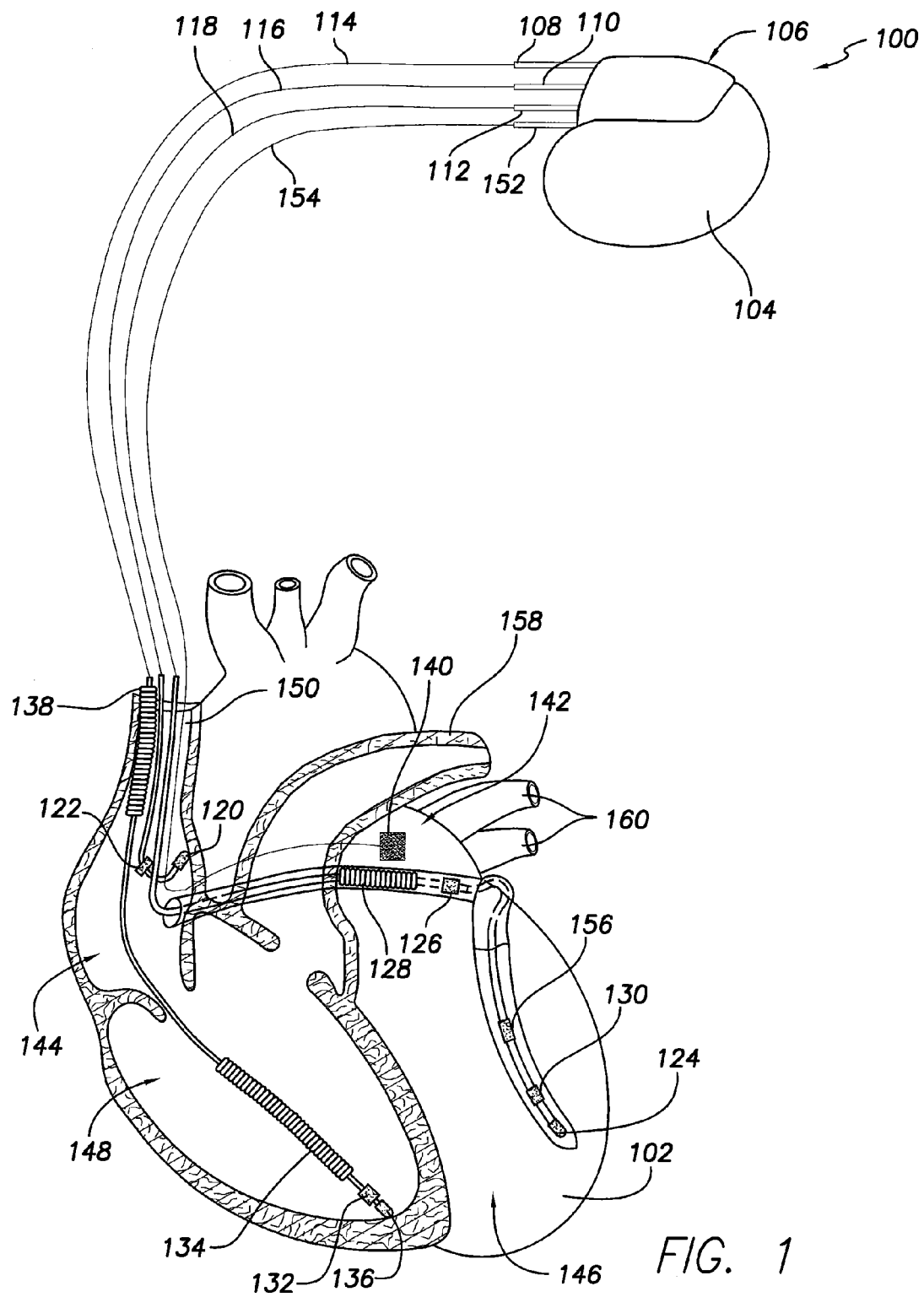
FIG. 1 illustrates an IMD that is implemented in accordance with one embodiment.

FIG. 1 illustrates an IMD 100 that is coupled to a heart 102. The IMD 100 may be a cardiac pacemaker, an ICD, a defibrillator, an ICD coupled with a pacemaker, a cardiac resynchronization therapy (CRT) pacemaker, a cardiac resynchronization therapy defibrillator (CRT-D), and the like, implemented in accordance with one embodiment of the present invention. The IMD 100 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. Alternatively, the IMD 100 may be a triple- or quad-chamber stimulation device. Optionally, the IMD 100 may be a multisite stimulation device capable of applying stimulation pulses to multiple sites within each of one or more chambers of the heart 102. As explained below in more detail, the IMD 100 may be controlled to obtain pressure measurements representative of a pressure in the superior vena cava, pulmonary artery, pulmonary vein, or any chamber of the heart 102 to apply or adjust a rate at which stimulation pulses applied to the heart 102 in order to reduce the pressure in the heart 102. The pressure measured by the IMD 100 may be an index of volume overload in one or more chambers 142-148 of the heart 102. For example, the pressure measured by the IMD 100 may be an indicator of atrial volume overload.

The IMD 100 includes a housing 104 that is joined to a header assembly 106 that holds receptacle connectors 108, 110, 112, 152 that are connected to a right ventricular lead 114, a right atrial lead 116, a coronary sinus lead 118, and a left atrial pressure sensing lead 154, respectively. By way of example only, the header assembly 106 may be an IS-4 connector assembly, although a different connector assembly may be used. A different number of connectors and/or leads may be included in the IMD 100. For example, the RV lead 114 may be joined to three connectors or ports in the IMD 100, with one connector or port electrically coupled with an SVC coil electrode 138, another connector or port coupled with an RV coil electrode 134, and another connector or port coupled with an RV tip electrode 136 and an RV ring electrode 132. In another example, the IMD 100 may include one or more dedicated leads in addition to, or in place of, one or more of the leads 114, 116, 118, 154. The dedicated leads may be electrically coupled to electrodes located in a chamber of the heart 102 such as the left atrium, a pulmonary vein, or the left ventricle. The electrodes may be dedicated electrodes that are provided to supply stimulation pulses to the heart 102 for pacing therapy, to sense cardiac signals of the heart 102 or to measure cardiac chamber pressure.

The leads 114, 116, 118, 154 may be located at various locations, such as an atrium 142, 144, a ventricle 146, 148, or both to measure physiological parameters of the heart 102. For example, a pressure sensor 140 may be coupled to the lead 154 to measure cardiac chamber pressure in the left atrium 142. One or more of the leads 114, 116, 118, 154 may detect IEGM signals that form an electrical activity indicator of myocardial function over multiple cardiac cycles. To sense atrial cardiac signals and to provide right atrial chamber stimulation therapy, the right atrial lead 116 has at least an atrial tip electrode 120, which typically is implanted in the right atrial appendage, and an atrial ring electrode 122.

The coronary sinus lead 118 receives atrial and ventricular cardiac signals and delivers left ventricular pacing therapy using at least a left ventricular ("LV") tip electrode 124. Optionally, the coronary sinus lead 118 may deliver left atrial ("LA") pacing therapy using at least a left atrial ring electrode 126. In one embodiment, the coronary sinus lead 118 delivers shocking therapy using at least an LA coil electrode 128. Alternatively, the LA coil electrode 128 may not be included in the IMD 100. The coronary sinus lead 118 also is connected with a plurality of LV ring electrodes 130, 156 disposed between the LV tip electrode 124 and the left atrial ring electrode 126. The LV ring electrode 130 may be used as a defibrillation electrode. The right ventricular ("RV") lead 114 has the RV tip electrode 136, the RV ring electrode 132, and the RV coil electrode 134. Optionally, the RV lead 114 may include the SVC coil electrode 138. The RV lead 114 is capable of delivering stimulation in the form of pacing and shock therapy to the right ventricle. The RV coil electrode 134 may be used as a defibrillation electrode.

A pressure sensor 140 may be provided in one or more chambers 142, 144, 146, 148 of the heart 102 to measure pressure within the respective chamber 142, 144, 146, 148. By way of example only, the pressure sensor 140 may be joined to the IMD 100 by providing the pressure sensor 140 on the lead 154. The lead 154 may be anchored in the interatrial septum of the heart 102 so that the pressure sensor 140 protrudes into the left atrium 142. Alternatively, the pressure sensor 140 may be provided on a different lead 114, 116, 118. While the pressure sensor 140 is located in the left atrial chamber 142 in the illustrated embodiment, the pressure sensor 140 may be disposed in another location to directly or indirectly obtain pressure measurements representative of a pressure in the heart 102. For example, the pressure sensor 140 may be provided in the right atrium 144, left ventricle 146, or right ventricle 148, and measure the pressure in the respective chamber 144-148. While only a single pressure sensor 140 is shown in FIG. 1, one or more additional pressure sensors 140 may be provided to obtain additional pressure measurements in the heart 102.

The pressure sensor 140 is schematically illustrated in FIG. 1 and may be embodied in a variety of sensors capable of directly or indirectly measuring fluid pressure in the heart 102. The pressure sensor 140 obtains a measurement of the pressure of blood in a chamber 142-148 of the heart 102 for each of a plurality of cardiac cycles in one embodiment. Alternatively, the pressure sensor 140 obtains a measurement of the pressure for a set of cardiac cycles. The pressure sensor 140 may obtain a single pressure measurement for a set of cardiac cycles, with the single pressure measurement being the result of a statistical function of the pressure measurements obtained during the set of cardiac cycles. For example, the pressure sensor 140 may obtain a pressure measurement for a set of cardiac cycles that is an average, mean, median, maximum, minimum, deviation, and the like, of the pressure measurements obtained during the set of cardiac cycles.

The pressure sensor 140 may include a pressure transducer that uses mechanical deflection of a diaphragm or spring to measure a pressure in the heart 102. In another example, the pressure sensor 140 may include a strain gauge that measures a change in resistance in a material of the sensor 140. The measured change in resistance is then correlated or mapped to a change in pressure in the heart 102 by the IMD 100. Alternatively, the sensor 140 may include a piezoresistive element that measures the change in conductivity of the element. The change in conductivity is then correlated or mapped to a change in pressure in the heart 102 by the IMD 100. The pressure sensor 140 may be a microelectromechanical system (MEMS) sensor. In another example, the sensor 140 may be a capacitance-based pressure sensor that measures a change in capacitance between opposing plates in the sensor 140. The change in capacitance is then correlated or mapped to a change in pressure in the heart 102 by the IMD 100.

In one embodiment, the pressure sensor 140 directly measures cardiac pressure in a chamber 142-148 of the heart 102 by locating the pressure sensor 140 in the chamber 142-148 and measuring the pressure in the corresponding chamber 142-148. For example, the pressure sensor 140 may be provided in the left atrium 142 or the right atrium 144 and directly measure the pressure in the left atrium 142 or the right atrium 144. Alternatively, the pressure sensor 140 may indirectly measure the fluid pressure in a chamber 142-148 by providing the pressure sensor 140 outside of the chamber of interest, measuring the pressure of the volume where the pressure sensor 140 is located, and mapping or correlating the measured pressure to the cardiac pressure of the chamber of interest. For example, the pressure sensor 140 may be provided in the left ventricle 146, right ventricle 148, superior vena cava 150, a pulmonary artery 158, a pulmonary vein 160, and the like. The pressure sensor 140 may then measure a cardiac pressure such as a right or left ventricular diastolic pressure, a pulmonary arterial diastolic pressure, or a pulmonary venous pressure. The measured pressure may then be correlated or mapped to a corresponding pressure in one or more of the chambers 142-148. Optionally, the pressure sensor 140 may be located outside of the cardiovascular system. For example, the pressure sensor 140 may include an ultrasound probe external to the IMD 100 and that indirectly measures a pressure in the heart 102 using ultrasound. The above examples are only provided to illustrate the variety of sensors and technologies that may be employed in the pressure sensor 140 and are not intended to limit the scope of the embodiments described herein.

The IMD 100 may reduce or prevent atrial volume overload by monitoring chamber pressure in the heart 102 and delivering pacing therapy to the heart 102 based on the pressure. The pacing therapy increases the rate at which stimulation pulses are applied to the heart 102 from an initial pacing rate to a peak, or target, pacing rate. The pacing therapy may reduce the cardiac chamber pressure in the heart 102 and may reduce or prevent atrial volume overload. As described above, reducing or preventing atrial volume overload may reduce or prevent atrial fibrillation and/or may result in atrial remodeling.

As described in more detail below, the IMD 100 reduces or prevents atrial volume overload by obtaining pressure measurements that are representative of a pressure in the heart 102, comparing the pressure measurements to a pressure threshold, and initiating, adjusting or terminating a pressure-reduction therapy in response thereto. The pressure-reduction therapy includes delivering stimulation pulses to the heart 102 at a pressure-based rate. The pressure-reduction therapy may include multi-side or multi-site atrial and/or ventricular pacing for example. The pressure-reduction therapy may increase the pressure-based rate from an initial pacing rate to a peak, or target, pacing rate during application of the therapy. The increased rate at which the stimulation pulses are applied may reduce the volume of fluid in the chambers 142-148 of the heart 102 and, in turn, reduce the volume overload in the chambers 142-148.

Figure 2:
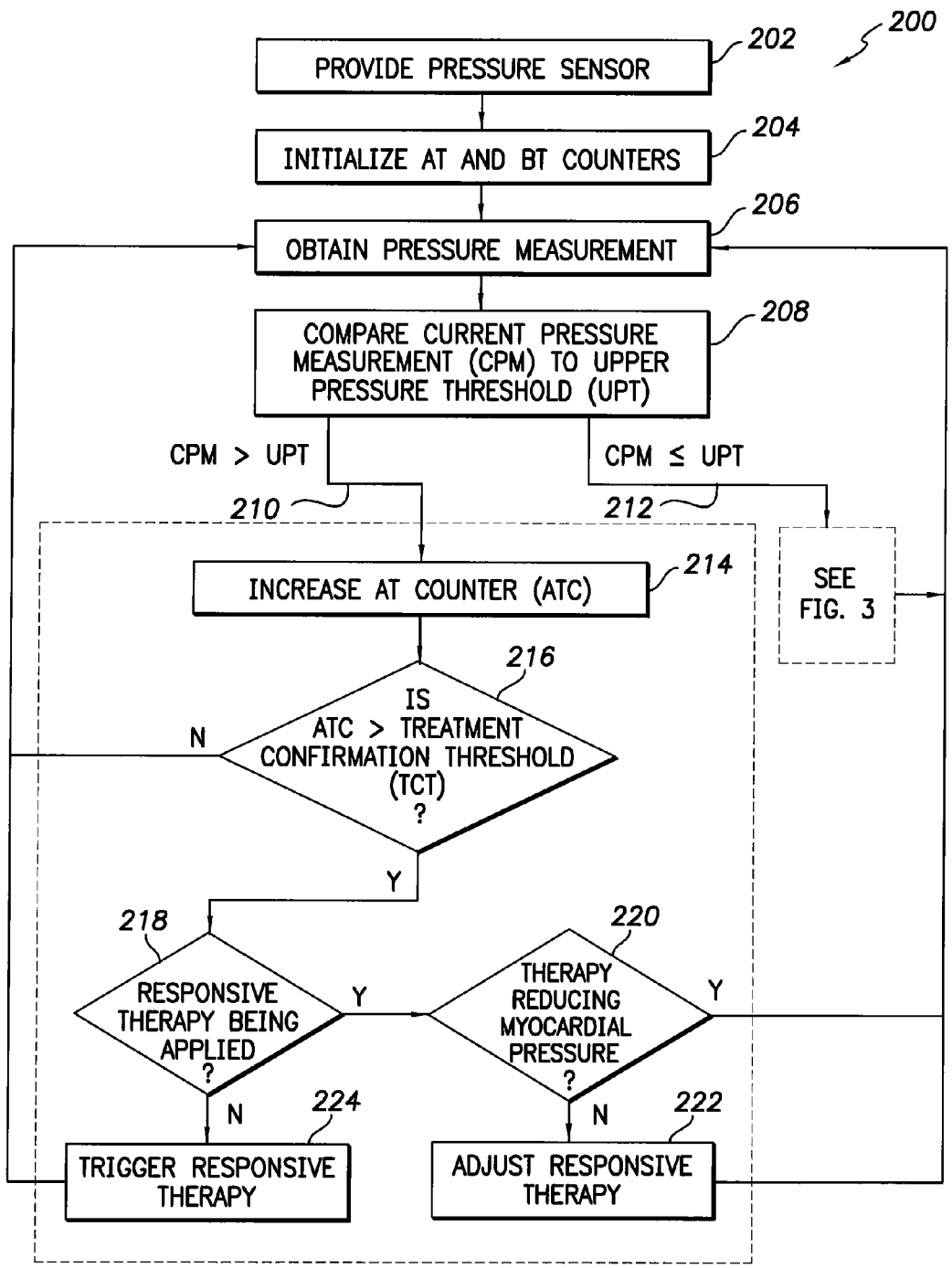
FIG. 2 illustrates a portion of a process implemented in accordance with one embodiment for reducing cardiac chamber pressure.
Figure 3:
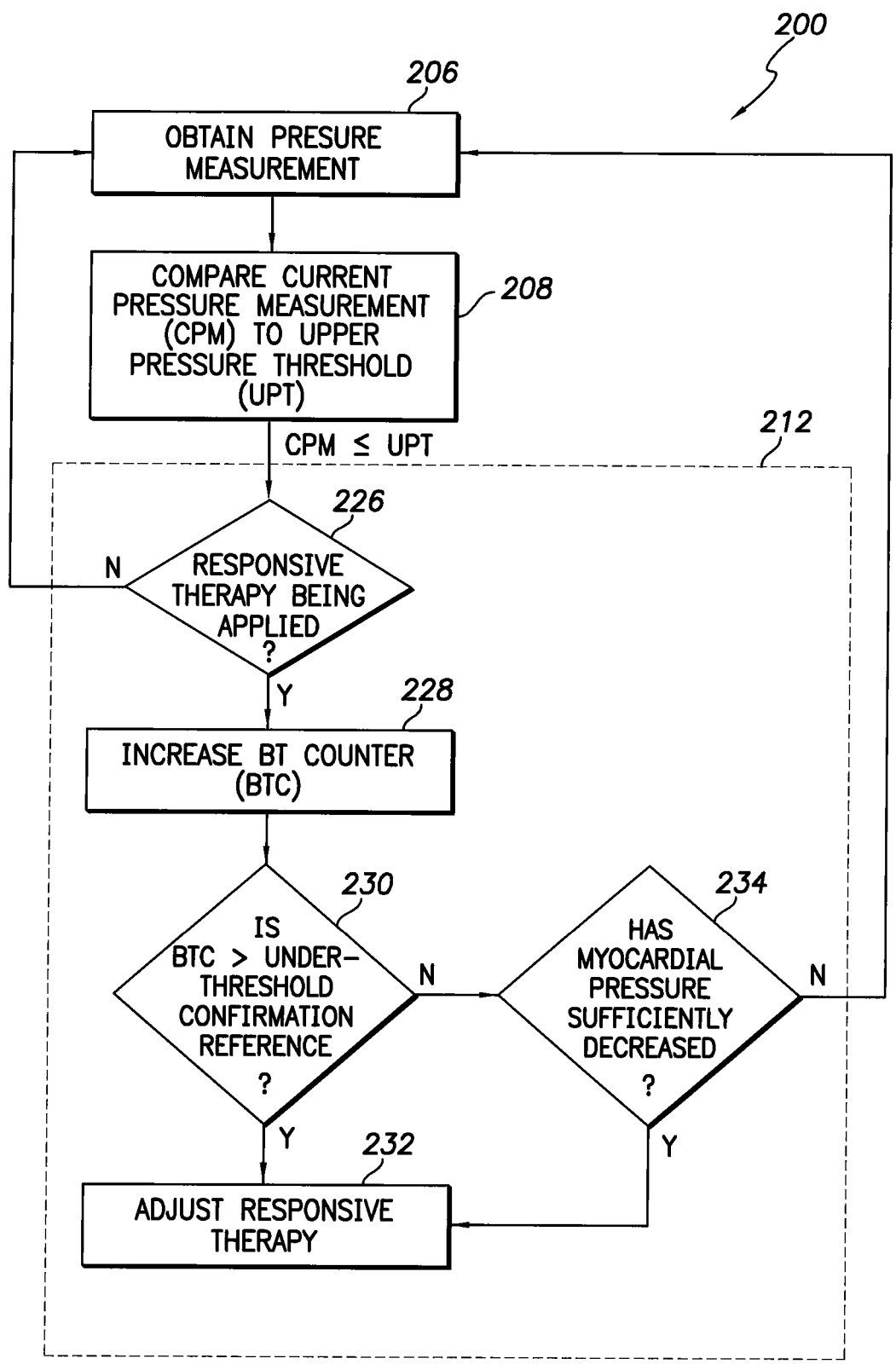
FIG. 3 illustrates another portion of the process implemented in accordance with one embodiment for reducing cardiac chamber pressure.

FIGS. 2 and 3 illustrate a process 200 for reducing pressure of the heart 102 (shown in FIG. 1). With respect to FIG. 2, at 202, a pressure sensor is provided in a position to measure pressure in the heart 102. For example, the pressure sensor 140 may be placed in one of the chambers 142-148 (shown in FIG. 1) of the heart 102. The pressure sensor 140 may be positioned to directly measure pressure in a chamber of interest in the heart 102. By way of example only, if a physician wishes to monitor the pressure in the right atrial chamber 144, the pressure sensor 140 may be placed in the right atrial chamber 144 to directly measure the pressure in the right atrial chamber 144. Alternatively, the pressure sensor 140 may be positioned to directly or indirectly measure pressure in a chamber of interest in the heart 102. For example, the pressure sensor 140 may be placed in a position outside of the right atrial chamber 144 and indirectly measure the pressure in the right atrial chamber 144. The pressure sensor 140 may indirectly measure the pressure by obtaining a pressure measurement outside of the chamber of interest and mapping or correlating the pressure measurement to the pressure in the chamber of interest. Optionally, the pressure sensor 140 may indirectly measure pressure in a chamber 142-148 while the pressure sensor 140 is located outside of the chambers 142-148. For example, the pressure sensor 140 may be provided in the superior vena cava 150 or outside of the heart 102.

At 204, an above-threshold counter (ATC) and a below-threshold counter (BTC) are initialized. The above- and below-threshold counters may be initialized by setting the values of each counter to zero. The above-threshold counter is used to count the number of pressure measurements that are above an upper pressure threshold 318 (shown in FIG. 4) and the below-threshold counter is used to count the number of pressure measurements that are below the upper pressure threshold 318. As described below, the upper pressure threshold 318 may be programmed by a physician or operator of the IMD 100 as a maximum cardiac chamber pressure to be exceeded before the responsive pressure-reduction therapy is initiated. The above- and below-threshold counters may be data entries stored in a computer-readable storage medium (e.g., memory 608 shown in FIG. 7) accessible by the IMD 100 (shown in FIG. 1).

At 206, a current pressure measurement is obtained by the pressure sensor 140 (shown in FIG. 1). The pressure measurement is representative of a pressure in a cardiac chamber. The pressure measurement obtained at 206 may be measured for a single cardiac cycle. As another example, a pressure measurement may be obtained for each cardiac cycle in a series of cardiac cycles. Alternatively, the pressure measurement may be obtained for each of non-consecutive cardiac cycles. By way of example only, the pressure measurement may be obtained for one of every N cardiac cycles, where N is an integer. Optionally, the pressure measurement obtained at 206 may be a statistical function of multiple pressure measurements obtained for multiple cardiac cycles. For example, the pressure measurement obtained at 206 may be a mean, average, median, maximum, minimum, deviation, running average, and the like, of multiple pressure measurements that are measured during a set of cardiac cycles.

Figure 4:
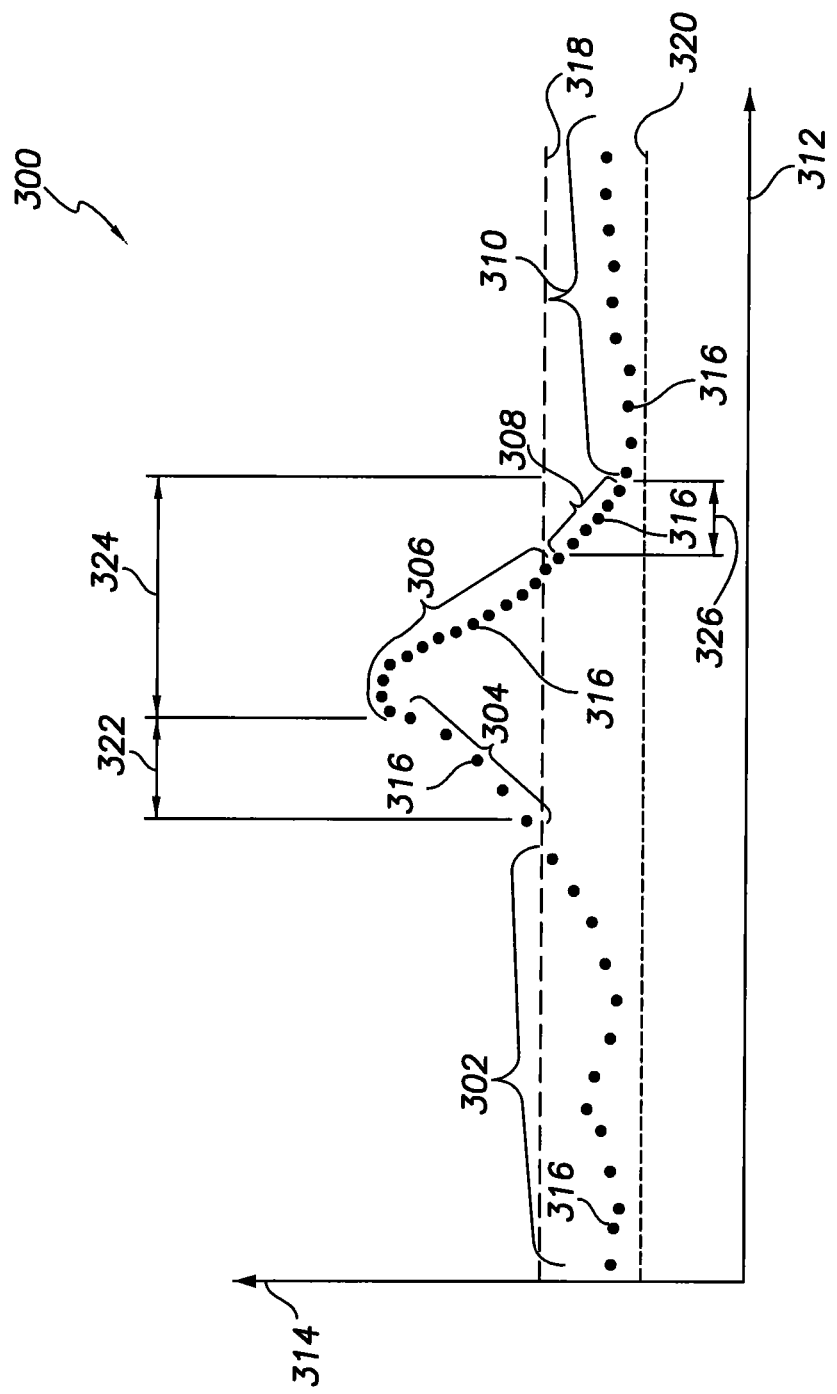
FIG. 4 illustrates graphical examples of pressure measurements obtained by a pressure sensor shown in FIG. 1.

The process of FIGS. 2 and 3 will be discussed in connection with FIG. 4. FIG. 4 is a graphical representation 300 of several pressure measurements 316 obtained by the pressure sensor 140 (shown in FIG. 1). A horizontal axis 312 represents time and a vertical axis 314 represents pressure. The pressure measurements 316 are individually obtained by the pressure sensor 140 during successive cardiac cycles. An upper pressure threshold 318 and a long term base pressure 320 are programmed and utilized to determine whether to trigger, adjust, or terminate a pressure-reduction therapy. The long term base pressure 320 may be a predetermined pressure of a cardiac chamber. The long term base pressure 320 may be set by a physician. Alternatively, the long term base pressure 320 may be a statistical function of pressure measurements obtained by the pressure sensor 140 (shown in FIG. 1). For example, the long term base pressure 320 may be one of a mean, median, average, maximum, minimum, deviation, and the like, of a set of previously measured cardiac chamber pressures. The long term base pressure 320 may be stored in a computer-readable storage medium that is accessible by the IMD 100, such as the memory 608 (shown in FIG. 7). The pressure-reduction therapy may be triggered when the pressure measurements 316 exceed the upper pressure threshold 318 for a predetermined time period or for a predetermined number of consecutive cardiac cycles 322. For example, the pressure-reduction therapy may be initiated when the pressure measurements 316 exceed the upper pressure threshold 318 for an amount of elapsed time that exceeds the predetermined time period. The amount of elapsed time may be measured by a clock 676 (shown in FIG. 7) disposed in the IMD 100.

The pressure-reduction therapy increases a rate at which stimulation pulses are delivered to the heart 102 (shown in FIG. 1) by the IMD 100 (shown in FIG. 1). The pressure-reduction therapy may be adjusted or terminated once the pressure in the heart 102 decreases below the upper pressure threshold 318 for a predetermined minimum number of consecutive cardiac cycles 326 or when the cardiac chamber pressure approaches the long term base pressure 320.

Each of the pressure measurements 316 are obtained, in turn, by the pressure sensor 140 at 206. For example, the process 200 may proceed by obtaining one of the pressure measurements 316 at 206, followed by examining the pressure measurement 316 and determining whether to initiate, adjust, or terminate the pressure-reduction therapy through the actions and determinations described below at 208-230. The process 200 may then return to 206 where the next pressure measurement 316 is obtained. Therefore, the process 200 may proceed in a loop-wise manner to obtain and examine each of the pressure measurements 316 in turn to determine whether the pressure-reduction therapy should be triggered, adjusted, or terminated.

Returning to FIGS. 2 and 3, at 208, the current pressure measurement 316 is compared to the upper pressure threshold 318 (shown in FIG. 4). The current pressure measurement 316 may be the most recently obtained pressure measurement 316 obtained by the pressure sensor 140 during the current cardiac cycle. As shown in FIG. 4, the pressure measurements 316 are arranged along the time axis 312 such that the pressure measurements 316 in the groups 302-310 are obtained in temporal order.

Depending on whether the current pressure measurement 316 exceeds the upper pressure threshold 318, the process 200 proceeds along one of separate logic paths 210, 212. If the current pressure measurement 316 exceeds the upper pressure threshold 318, then the process 200 continues along the logic path 210 shown in FIG. 2. Alternatively, if the current pressure measurement 316 does not exceed the upper pressure threshold 318, then the process continues along a different logic path 212 shown in FIG. 3.

With respect to the first logic path 210, at 214, the above-threshold counter (ATC) is increased. For example, the above-threshold counter may be incrementally increased in value by one. The above-threshold counter is increased to indicate the number of pressure measurements 316 that have been found to be greater than the upper pressure threshold 318 since the above-threshold counter has been reset or initialized. In one embodiment, the above-threshold counter represents the number of consecutive pressure measurements 316 that exceed the upper pressure threshold. For example, the above-threshold counter may indicate the number of consecutive cardiac cycles having a cardiac chamber pressure that exceeds the upper pressure threshold 318. The above-threshold counter may be reset once a cardiac cycle does not exhibit a cardiac chamber pressure that exceeds the upper pressure threshold 318.

At 216, a determination is made as to whether the above-threshold counter exceeds a treatment confirmation threshold (TCT). The treatment confirmation threshold represents a minimum number of pressure measurements 316 that exceed the upper pressure threshold 318 before a pressure-reduction therapy is initiated. For example, the treatment confirmation threshold may be a predetermined minimum number of consecutive cardiac cycles with pressure measurements 316 that must exceed the upper pressure threshold 318 before the pressure-reduction therapy begins. Alternatively, the treatment confirmation threshold may be an amount of time that consecutive pressure measurements 316 exceed the upper pressure threshold 318 before the pressure-reduction therapy is initiated. The treatment confirmation threshold may be stored in the memory 608 (shown in FIG. 7). The treatment confirmation threshold may be adjustable by a physician or other operator of the IMD 100.

The above-threshold counter may be compared to the treatment confirmation threshold to avoid prematurely initiating the pressure-reduction therapy. For example, the pressure in a chamber 142-148 (shown in FIG. 1) may vary with respect to time. The pressure may occasionally exceed the upper pressure threshold 318 for a relatively short amount of time, such as a few cardiac cycles, before returning below the upper pressure threshold 318. In accordance with one embodiment, in order to avoid prematurely triggering initiation of the pressure-reduction therapy, a minimum number of consecutive cardiac cycles exhibit pressure measurements 316 exceed the upper pressure threshold 318 before triggering the pressure-reduction therapy. If the above-threshold counter exceeds the treatment confirmation threshold, then the process 200 continues to 218. Alternatively, if the above-threshold counter does not exceed the treatment confirmation threshold, then the process 200 returns to 206 where the pressure measurement 316 is obtained.

In another embodiment, the amount of time that consecutive pressure measurements 316 have exceeded the upper pressure threshold 318 may be compared to the treatment confirmation threshold to avoid prematurely initiating the pressure-reduction therapy. If the amount of time, during which the pressure measurements 316 have been greater than the upper pressure threshold 318, exceeds the treatment confirmation threshold, then the process 200 continues to 218. Alternatively, if the amount of time, during which the pressure measurements 316 have been greater than the upper pressure threshold 318, does not exceed the treatment confirmation threshold, then the process 200 returns to 206 where the pressure measurement 316 is obtained.

At 218, a determination is made as to whether the pressure-reduction therapy is currently being applied to the heart 102 (shown in FIG. 1). The determination may include an examination of the current, pressure-based rate at which stimulation pulses are applied to the heart 102 by the IMD 100 (shown in FIG. 1). For example, the determination may examine the current pressure-based rate at which stimulation pulses are supplied by the IMD 100 to decide whether the current rate is greater than an initial pacing rate of the IMD 100. Alternatively, the determination may include a decision as to whether the current pressure-based pacing rate for the current cardiac cycle is greater than the pacing rate for one or more previous cardiac cycles. The initial pacing rate may include the rate at which stimulation pulses are normally applied to the heart 102 by the IMD 100. For example, the initial pacing rate may be the rate that the IMD 100 applies to the heart 102 prior to initiating the process 200. The initial pacing rate may be stored in memory and may be established by a physician or operator of the IMD 100.

If, at 218, it is determined that the pressure-reduction therapy already is being applied to the heart 102 (shown in FIG. 1), a check on the effectiveness of the pressure-reduction therapy is performed at 220. For example, if the pressure-reduction therapy is being applied to the heart 102, the current pressure measurement 316 may be examined to determine if the pressure-reduction therapy is lowering the cardiac chamber pressure. The difference between the current pressure measurement 316 and the upper pressure threshold 318 may be compared to a predetermined pressure deviation threshold. For example, if the difference between the current pressure measurement 316 and the upper pressure threshold 318 exceeds the pressure deviation threshold, then the pressure-reduction therapy may be determined to not be effectively decreasing cardiac chamber pressure.

In another example, the current pressure measurement 316 may be compared to the previous pressure measurements 316 to determine if a downward trend exists in the pressure measurements 316. The trend may be calculated from a set or subset of pressure measurements 316 obtained since the pressure-reduction therapy was initiated. The trend in the pressure measurements 316 may be determined using a statistical function or model, such as a least squares model, a weighted least squares model, an R-squared model, an autoregressive moving average model, or a generalized linear model. If the trend demonstrates that the pressure measurements 316 that are obtained since initiation of the pressure-reduction therapy are decreasing, then the pressure-reduction therapy may be changed or ceased. On the other hand, the pressure-reduction therapy may not be effectively reducing cardiac chamber pressure if the trend does not demonstrate that the pressure measurements 316 are decreasing.

Alternatively, the current pressure measurement 316 may be compared to a statistical function of one or more previous pressure measurements 316 obtained during the pressure-reduction therapy. For example, the current pressure measurement 316 may be compared to one or more of an average, median, mean, deviation, maximum, minimum, and the like, of the pressure measurements 316 obtained since initiation of the pressure-reduction therapy. The pressure measurements 316 may be stored in memory. If the current pressure measurement 316 is less than the statistical function of the previous pressure measurements 316 obtained during the pressure-reduction therapy, then it may be determined that the pressure-reduction therapy is effectively decreasing cardiac chamber pressure. On the other hand, the pressure-reduction therapy may not be effectively decreasing cardiac chamber pressure if the current pressure measurement 316 is equal to or greater than the statistical function of the previous pressure measurements 316 obtained during the pressure-reduction therapy.

If, at 220, it is determined that the pressure-reduction therapy is reducing cardiac chamber pressure, the process 200 may return to 206 where the next pressure measurement 316 is obtained. Alternatively, if, at 220, it is determined that the pressure-reduction therapy is not reducing cardiac chamber pressure, the pressure-reduction therapy may be adjusted at 222.

At 222, the pressure-reduction therapy is adjusted. For example, a target, or peak, rate at which the stimulation pulses are applied to the heart 102 (shown in FIG. 1) during the pressure-reduction therapy may be increased. In another example, the rate of acceleration in which the pacing rate of the IMD 100 (shown in FIG. 1) is increased from an initial pacing rate to the peak, or target, rate may be increased, as described below. The process 200 may then return to 206 where the next pressure measurement is obtained.

Returning to the determination made at 218, if the pressure-reduction therapy is not being applied, then the pressure-reduction therapy is initiated at 224. As described below, the pressure-reduction therapy may be initiated by immediately increasing the pressure-based rate at which the stimulation pulses are applied to the heart 102 from an initial pacing rate to a target, or peak, pacing rate. Alternatively, the pressure-reduction therapy may be initiated by gradually increasing the pressure-based rate at which the stimulation pulses are applied to the heart 102 from an initial pacing rate to the peak or target rate along one or more acceleration curves, or rates, as described below. After initiating the pressure-reduction therapy, the next pressure measurement 316 is obtained at 206.

The process 200 may proceed in a loop-wise manner through the actions and determinations described above at 206-210 and 214-224 to obtain pressure measurements 316 until a minimum number of consecutive pressure measurements 316 exceeds the upper pressure threshold 318. Once the minimum number of pressure measurements 316 exceeds the upper pressure threshold 318, or the length of time that consecutive pressure measurements 316 have exceeded the upper pressure threshold 318 exceeds a predetermined amount of time, the pressure-reduction therapy is triggered or, if the pressure-reduction therapy has been triggered, the additional pressure measurements 316 are obtained to examine the impact of the pressure-reduction therapy on the cardiac chamber pressure.

Returning to 208, if the current pressure measurement 316 does not exceed the upper pressure threshold, then the process 200 proceeds along the second logic path 212. The process of the second logic path 212 is shown in FIG. 3. At 226, a determination is made as to whether the pressure-reduction therapy is currently occurring. If the pressure-reduction therapy is not being applied to the heart 102, then the process 200 returns to 206 where the next pressure measurement 316 is obtained. Alternatively, if the pressure-reduction therapy is being applied, then the below-pressure counter is increased at 228. For example, a value of one may be added to the below-pressure counter. The below-pressure counter represents the number of pressure measurements 316 that do not exceed the upper pressure threshold 318 and that are obtained after triggering the pressure-reduction therapy. The below-pressure counter may indicate the number of consecutive cardiac cycles occurring during the pressure-reduction therapy and exhibiting pressure measurements 316 below the upper pressure threshold 318.

At 230, a determination is made as to whether the below-threshold counter exceeds an under-threshold confirmation reference. The under-threshold confirmation reference represents a number of pressure measurements 316 that do not exceed the upper pressure threshold 318 before the pressure-reduction therapy is adjusted. For example, the under-threshold confirmation reference may be a minimum number of consecutive cardiac cycles with pressure measurements 316 that do not exceed the upper pressure threshold 318 before the pressure-reduction therapy ceases or is terminated. Alternatively, the under-threshold confirmation reference may be a minimum number of consecutive cardiac cycles with pressure measurements 316 that do not exceed the upper pressure threshold 318 before the rate at which stimulation pulses are applied during the pressure-reduction therapy is decreased or otherwise adjusted.

As described above, the pressure in a chamber 142-148 (shown in FIG. 1) may vary with respect to time. The pressure may occasionally fall below the upper pressure threshold 318 for a relatively short amount of time, such as a few cardiac cycles, before again increasing above the upper pressure threshold 318. In one embodiment, in order to avoid prematurely terminating or adjusting the pressure-reduction therapy, the pressure-reduction therapy may continue to be applied until a minimum number of consecutive cardiac cycles exhibit pressure measurements 316 that do not exceed the upper pressure threshold 318. The under-threshold confirmation reference may be stored in memory 608 and established by a physician or other operator of the IMD 100.

If the below-threshold counter is found to exceed the under-threshold confirmation reference at 230, then at 232 the pressure-reduction therapy is adjusted. The pressure-reduction therapy may be adjusted by terminating the pressure-reduction therapy or by reducing the rate at which stimulation pulses are applied to the heart 102 (shown in FIG. 1) by the pressure-reduction therapy. For example, if the pressure in the cardiac chamber has fallen below the upper pressure threshold 318 for a predetermined minimum number of consecutive cardiac cycles, then the process 200 determines that the pressure-reduction therapy has sufficiently reduced the cardiac chamber pressure for a minimum amount of time or a minimum number of cardiac cycles. Once the cardiac chamber pressure has been reduced below the upper pressure threshold for the minimum amount of time or cardiac cycles, then the process 200 determines that continued application of the pressure-reduction therapy is no longer required or may need to be adjusted. For example, the pressure-reduction therapy may be terminated by immediately reducing the rate at which stimulation pulses are delivered to the heart 102 by the IMD 100 (shown in FIG. 1) from the pressure-based rate to the initial pacing rate of the IMD 100, as described below. Alternatively, the pressure-reduction therapy may be terminated by gradually reducing the rate at which stimulation pulses are delivered to the heart 102 by the IMD 100 from the current pressure-based rate or the peak rate to the initial pacing rate of the IMD 100 along one of several deceleration rates, as described below.

If the below-threshold counter is found to not exceed the under-threshold confirmation reference at 230, then at 234 a determination is made as to whether the cardiac chamber pressure has sufficiently decreased. The determination may include a comparison between the current pressure measurement 316 and the long term base pressure 320. The current pressure measurement 316 may be compared to the long term base pressure 320 to determine if the current pressure measurement 316 is approaching the long term base pressure 320. By way of example only, the comparison between the current pressure measurement 316 and the long term base pressure 320 may include a decision as to whether the current pressure measurement 316 is within one of 110%, 120%, 150%, and the like, of the long term base pressure 320. Comparing the current pressure measurement 316 to the basal pressure 316 permits the process 200 to determine if the pressure measurements 316 are approaching the long term base pressure 320 before the current pressure measurements 316 fall below the long term base pressure 320.

If it is determined that the cardiac chamber pressure has sufficiently decreased at 234, then the pressure-reduction therapy is adjusted or terminated at 232. Alternatively, if it is determined at 234 that the cardiac chamber pressure has not sufficiently decreased, then the next pressure measurement 316 is obtained at 206. The process 200 may proceed in a loop-wise manner through the actions and determinations described above at 206-208 and 226-234. Once a minimum number of pressure measurements 316 are collected that do not exceed the upper pressure threshold 318 or the pressure measurements 316 approach the long term base pressure 320, then the pressure-reduction therapy may be terminated or adjusted.

Returning to FIG. 4, the process 200 will proceed through each of the pressure measurements 316 in turn to determine whether to apply, adjust or terminate the pressure-reduction therapy applied to the heart 102. The process 200 after analyzing the pressure measurements 316 in the first group 302 would determine that none of the first group pressure measurements 316 exceeds the upper pressure threshold 318. When analyzing the second group 304, the process 200 would determine that each of the pressure measurements 316 exceeds the upper pressure threshold 318. As each pressure measurement 316 in the second group 304 is examined, the above-threshold counter may be incrementally increased until the above-threshold counter exceeds the treatment confirmation threshold. The time period, over which the pressure measurements 316 exceed the upper pressure threshold 318 and the above-threshold counter is increased, may be referred to as a treatment confirmation window 322. Once the above-threshold counter exceeds the treatment confirmation threshold, the pressure-reduction therapy is triggered (at 218, 224). For example, if the treatment confirmation threshold has a value of five, the process 200 may initiate the pressure-reduction therapy when the sixth consecutive pressure measurement 316 exceeds the upper pressure threshold 318. The third group 306 of pressure measurements 316 begins with the sixth consecutive pressure measurement 316 that exceeds the upper pressure threshold 318. The pressure-reduction therapy therefore may be initiated when the first pressure measurement 316 in the third group 306 is obtained. As the pressure-reduction therapy is applied, the pressure measurements 316 in the third group 306 gradually decrease in value, as shown in FIG. 4. The time period over which the pressure-reduction therapy is applied is referred to as a therapy window 324. Once the pressure measurements 316 decrease to a value that does not exceed the upper pressure threshold 318, the process 200 enters an under-threshold treatment continuity window 326, where it is determined whether to adjust or terminate the pressure-reduction therapy. The time period over which the process 200 continues to apply the pressure-reduction therapy after the pressure measurements 316 have fallen below the upper pressure threshold 318 may be referred to as an under-threshold treatment continuity window 326.

In the fourth group 308 of pressure measurements 316, the process 200 determines that each of the pressure measurements 316 does not exceed the upper pressure threshold 318. As each of the fourth group pressure measurements 316 is examined, the below-threshold counter may be incrementally increased until the below-threshold counter exceeds the under-threshold confirmation reference. Once the below-threshold counter exceeds the under-threshold confirmation reference, the pressure-reduction therapy is adjusted (at 230, 232). The pressure-reduction therapy may be adjusted by decreasing the rate at which stimulation pulses are supplied to the heart 102 or by terminating the pressure-reduction therapy. The process 200 may continue to apply the pressure-reduction therapy even after the cardiac chamber pressure falls below the upper pressure threshold 318 for the continuity window 326. The process 200 may continue to apply the pressure-reduction therapy for a predetermined number of cardiac cycles to prevent the cardiac chamber pressure from immediately increasing again above the upper pressure threshold 318.

Optionally, the process 200 may adjust the pressure-reduction therapy when the cardiac chamber pressure approaches the long term base pressure 320 (at 234). For example, the process 200 may terminate the pressure-reduction therapy when the cardiac chamber pressure is less than or equal to 110% of the long term base pressure 320. As a result, if a sixth pressure measurement 316 in the fourth group 308 of pressure measurements 316 is less than or equal to 110% of the long term base pressure 320, then the process 200 may adjust the pressure-reduction therapy.

The fifth group 310 of pressure measurements 316 begins when the pressure-reduction therapy has been adjusted. The process 200 may continue obtaining pressure measurements 316, comparing the pressure measurements 316 to the upper pressure threshold 318, and determining whether to initiate, adjust or terminate the pressure-reduction therapy based on the pressure measurements 316.

As described above, the pressure-reduction therapy may include increasing the rate at which stimulation pulses are applied to the heart 102 (shown in FIG. 1) by the IMD 100 (shown in FIG. 1). The pressure-reduction therapy may increase the pressure-based rate at which stimulation pulses are applied from the initial pacing rate of the IMD 100 to a peak, or target, pacing rate. In one embodiment, the peak rate is greater than the pacing rate of the IMD 100. For example, the peak rate may be approximately 90 beats per minute or more. The peak or target rate may be stored on the memory 608 (shown in FIG. 7). The peak rate may be predetermined by a physician or operator of the IMD 100. The peak rate may be adjusted based on the patient in whom the IMD 100 is implanted. For example, for older patients or patients exhibiting significant coronary disease or myocardial instability, the peak rate may be set to be less than the pressure-based rate for younger patients or patients exhibiting lesser coronary disease or myocardial instability.

Figure 5:
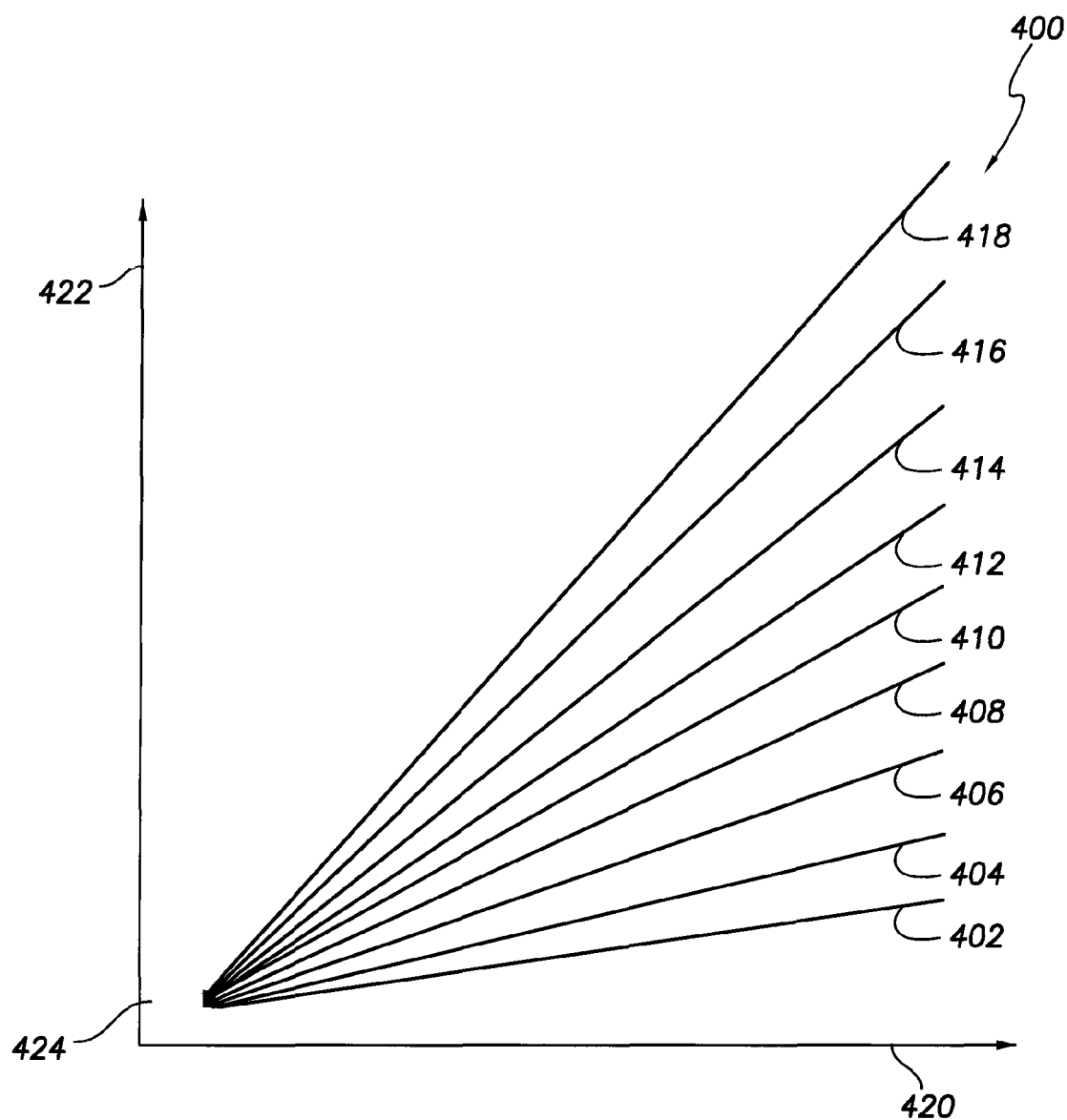
FIG. 5 illustrates graphical examples of pacing acceleration rates according to one embodiment.

FIG. 5 is a graphical representation 400 of several pacing acceleration rates 402-418 according to one embodiment. A horizontal axis 420 represents time and a vertical axis 422 represents a rate at which stimulation pulses are applied to the heart 102 by the IMD 100. The pressure-based rate at which stimulation pulses are applied to the heart 102 may be increased along one or more of the pacing acceleration rates 402-418 during the pressure-reduction therapy. The pacing acceleration rates 402-418 may increase from an initial pacing rate 424 and increase along one or more of the acceleration rates 402-418. In the illustrated embodiment, the pressure-based rate may be accelerated more quickly for the acceleration rates 412-418 than for the acceleration rates 402-410. While the acceleration rates 402-418 are illustrated as approximately straight lines with respect to time in the illustrated embodiment, the acceleration rates 402-418 may be embodied in different curves or shapes. For example, the acceleration rates 402-418 may increase with respect to time along an exponential curve, a logarithmic curve, or some other mathematical curve. The acceleration rates 402-418 may increase to an asymptote. The acceleration rates 402-418 may be stored in memory and may be established by a physician or operator of the IMD 100.

The acceleration rates 402-418 may be adjusted based on the patient in whom the IMD 100 is implanted. For example, for older patients or patients exhibiting significant coronary disease or myocardial instability, a lesser acceleration rate 402-418 may be used when compared to the acceleration rate 402-418 used for younger patients or patients exhibiting lesser coronary disease or myocardial instability.

Figure 6:
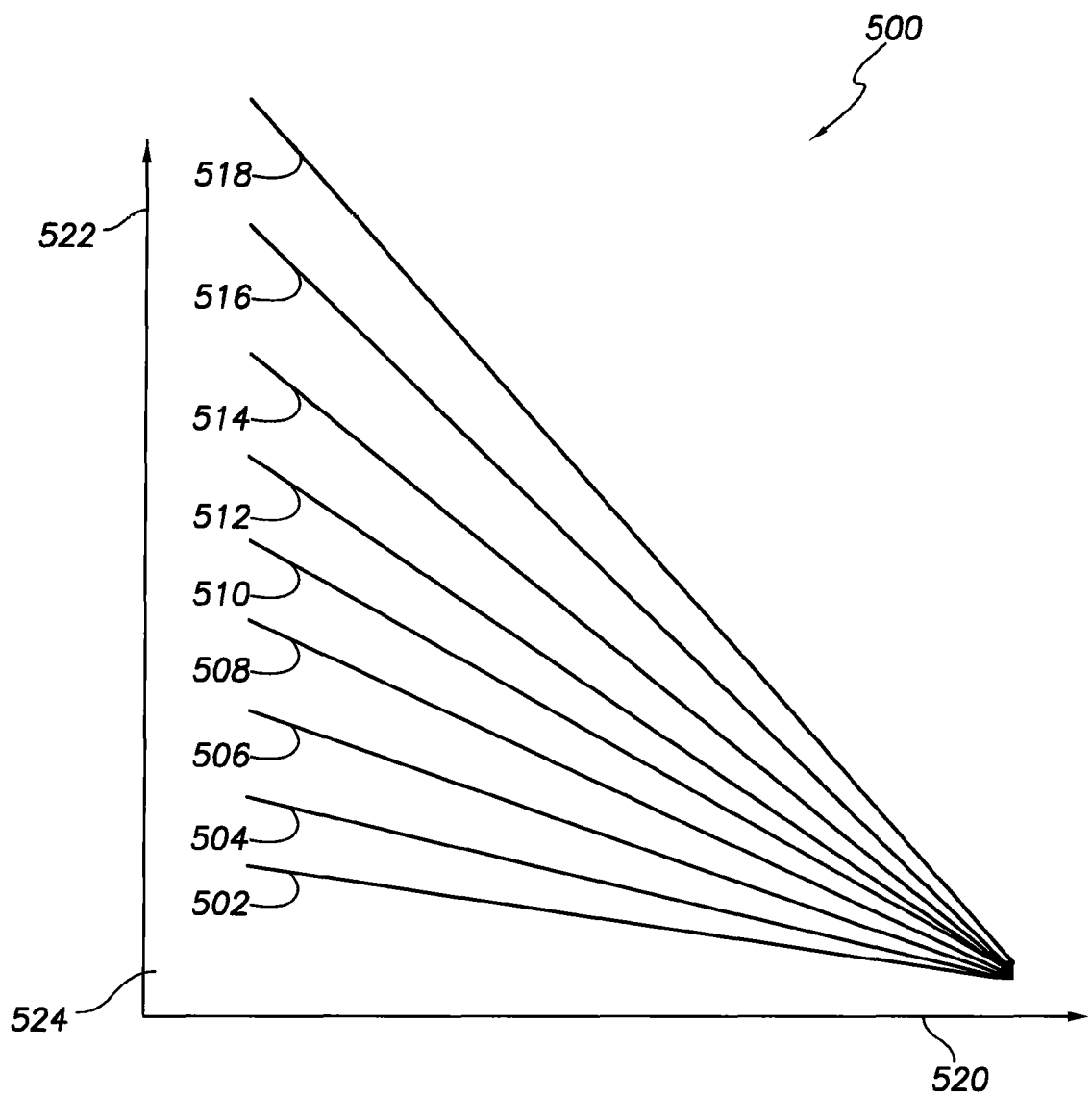
FIG. 6 illustrates graphical examples of pacing deceleration rates according to one embodiment.

FIG. 6 is a graphical representation 500 of several pacing deceleration rates 502-518 according to one embodiment. A horizontal axis 520 represents time and a vertical axis 522 represents a rate at which stimulation pulses are applied to the heart 102. Upon termination of the pressure-reduction therapy, the pressure-based rate at which stimulation pulses are applied to the heart 102 may be decreased along one or more of the pacing deceleration rates 502-518. The pacing deceleration rates 502-518 may be opposite that of the acceleration rates 402-418 shown in FIG. 5. The pacing deceleration rates 502-518 may begin at the peak rate and decrease along one or more of the deceleration rates 502-518. Alternatively, the pacing deceleration rates 502-518 may begin at a current pressure-based rate that is less than the peak rate and decrease with respect to time along one or more of the deceleration rates 502-518. As the pressure-reduction therapy is terminated, the rate of the stimulation pulses may be decreased to the initial pacing rate 524. The relationships between time and rate illustrated by the deceleration rates 502-518 in FIG. 6 are provided merely for illustration and are not intended to be limiting and the deceleration rates 502-518 may be embodied in different curves or mathematical functional shapes. The deceleration rates 502-518 may be stored in memory and established by a physician or operator of the IMD 100. The deceleration rates 502-518 may be adjusted based on the patient in whom the IMD 100 is implanted. For example, for older patients or patients exhibiting significant coronary disease or myocardial instability, a lesser deceleration rate 502-518 may be used when compared to the deceleration rate 502-518 used for younger patients or patients exhibiting lesser coronary disease or myocardial instability.

Figure 7:
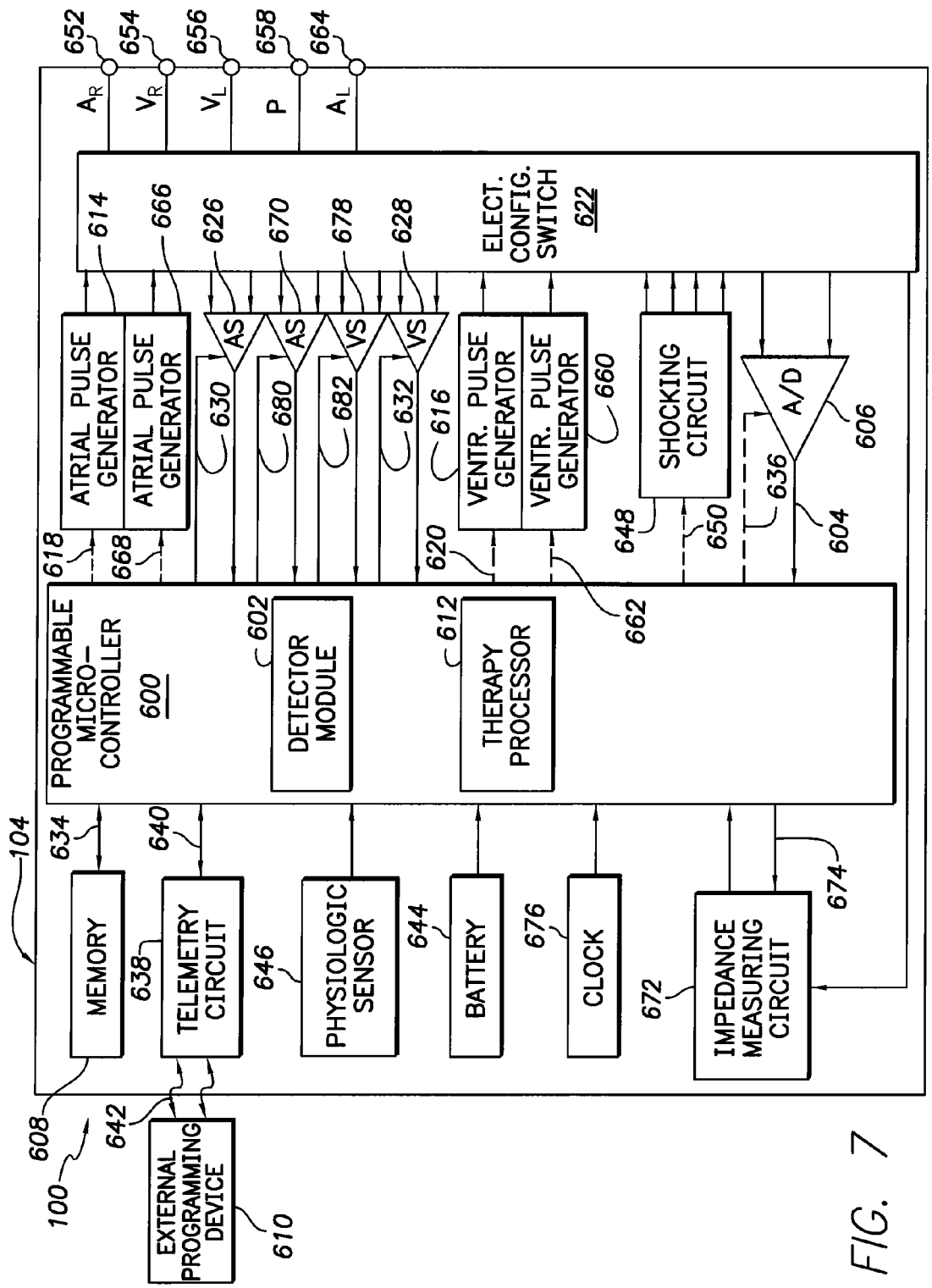
FIG. 7 illustrates a block diagram of internal components of the IMD shown in FIG. 1 according to one embodiment.

FIG. 7 illustrates a block diagram of exemplary internal components of the IMD 100. The IMD 100 is for illustration purposes only, and it is understood that the circuitry could be duplicated, eliminated, or disabled in any desired combination to provide a device capable of treating the appropriate chamber(s) of the heart with cardioversion, defibrillation, and/or pacing stimulation. As described above, the IMD 100 may be used to measure cardiac chamber pressure and trigger, adjust or terminate a pressure-reduction therapy in response to increasing cardiac chamber pressure. The IMD 100 may perform one or more of the actions described above in connection with the process 200 (shown in FIGS. 2 and 3).

The housing 104 for the IMD 100 is often referred to as the "can", "case", or "case electrode" and may be programmably selected to act as the return electrode for all "unipolar" and defibrillation modes. The housing 104 further includes a connector (not shown) having a plurality of inputs. The inputs may include one or more of a right atrial input terminal ($A_R$) 652, a right ventricular input terminal ($V_R$) 654, a left ventricular input terminal ($V_L$) 656, a pressure sensing input terminal (P) 658, and a left atrial input terminal ($A_L$) 664. The right atrial input terminal 652 may be electrically coupled to the right atrial tip electrode 120 (shown in FIG. 1) and the right atrial ring electrode 122 (shown in FIG. 1). The right ventricular input terminal 654 may be electrically coupled to the right ventricular tip electrode 136 (shown in FIG. 1), the right ventricular ring electrode 132 (shown in FIG. 1), the right ventricular coil electrode 134 (shown in FIG. 1) and the SVC coil electrode 138 (shown in FIG. 1). The left ventricular input terminal 656 may be electrically coupled to the left ventricular tip electrode 124 (shown in FIG. 1) and one or more of the left ventricular ring electrodes 130, 156 (shown in FIG. 1). The left atrial input terminal 664 may be coupled with a plurality of left atrial ring electrodes 126 (shown in FIG. 1) and/or the left atrial coil electrode 128 (shown in FIG. 1). Optionally, one or more of the left atrial ring electrodes 126 and the left atrial coil electrode 128 may be coupled with the left ventricular input terminal 656. The pressure sensing input terminal 658 may be electrically coupled to the pressure sensor 140 (shown in FIG. 1). The IMD 100 may include additional input terminals not illustrated in FIG. 7, such as an input terminal coupled to lead extending into the coronary sinus and joined to an electrode placed in the oblique vein of the left atrium 142, or the oblique vein of Marshall, to sense and pace the left atrium 158.

The IMD 100 includes a programmable microcontroller 600, which controls the operation of the IMD 100 based on acquired cardiac signals and on the pressure measurements 316. The microcontroller 600 (also referred to herein as a processor, processor module, or unit) typically includes a microprocessor, or equivalent control circuitry, and may be specifically designed for controlling the delivery of stimulation therapy and may further include RAM or ROM memory, logic and timing circuitry, state machine circuitry, and I/O circuitry. Among other things, the microcontroller 600 receives, processes, and manages storage of digitized data from the various electrodes 124-138 (shown in FIG. 1) and the pressure sensor 140. The microcontroller 600 may include one or more modules and processors configured to perform one or more of the actions and determinations described above in connection with the process 200. A detector module 602 may communicate with the pressure sensor 140 to receive the pressure measurements 316. The detector module 602 may communicate with the pressure sensor 140 via a pressure data signal 604 from an analog-to-digital (A/D) data acquisition system 606. The pressure signals obtained by the pressure sensor 140 are applied to the inputs of the data acquisition system 606. The data acquisition system 606 convert the raw analog data of the pressure signals into a digital pressure measurement signal, and communicates the pressure measurement signals as pressure measurements 316 to the detector module 602 via the data signal 604. A control signal 636 from the microcontroller 600 determines when the data acquisition system 606 acquires signals, stores the signals in the memory 608, or transmits data to the external device 610.

The detector module 602 compares the pressure measurements 316 to one or more of the upper pressure threshold 318 and the long term base pressure 320, as described above. The detector module 602 communicates the results of the comparison to a therapy processor 612. The therapy processor 612 receives the comparison between the pressure measurement 316 and the upper pressure threshold 318 and/or the long term base pressure 320 and instructs an excitation source to deliver stimulation pulses to the heart 102 at the pressure-based rate, as described above. The excitation source may include first and second atrial pulse generators 614, 666 and first and second ventricular pulse generators 616, 660 to generate the stimulation pulses. In order to provide stimulation therapy in each of the chambers 142-148 of the heart 102, the atrial and ventricular pulse generators 614, 666 and 616, 660 may include dedicated, independent pulse generators, multiplexed pulse generators, or shared pulse generators. The pulse generators 614, 666 and 616, 660 are controlled by the microcontroller 600 via appropriate control signals 618, 668 and 620, 662 respectively, to trigger or inhibit the stimulation pulses. The stimulation pulses that are applied to the heart 102 may be generated by one or more of the atrial and ventricular pulse generators 614, 666 and 616, 660.

The clock 676 is communicatively coupled to the microcontroller 600. The clock 676 measures an elapsed amount of time based on start and stop control signals from the microcontroller 600. For example, the clock 676 may begin measuring the elapsed amount of time when the pressure measurements 316 (shown in FIG. 4) first exceed the upper pressure threshold 318 (shown in FIG. 4) and the microcontroller 600 sends the start signal to the clock 676. Similarly, the clock 676 may cease measuring the elapsed amount of time when the pressure-reduction therapy terminates and the microcontroller 600 sends the stop signal to the clock 676.

Switch 622 includes a plurality of switches for connecting the desired electrodes, including the electrodes 124-138 to the appropriate I/O circuits, thereby providing complete electrode programmability. The switch 622, in response to a control signal 624 from the microcontroller 600, determines the polarity of stimulation pulses (e.g., unipolar, bipolar, etc.) by selectively closing the appropriate combination of switches (not shown). First and second atrial sensing circuits 626, 670 and first and second ventricular sensing circuits 628, 678 also may be selectively coupled to the leads 114, 116, 118, 154 through the switch 622 for detecting the presence of cardiac activity in each of the chambers 142-148 (shown in FIG. 1) of the heart 102 (shown in FIG. 1). Control signals 630, 632, 680, 682 from microcontroller 600 direct output of the atrial and ventricular sensing circuits 626, 670 and 628, 678 that are connected to the microcontroller 600. In this manner, the atrial and ventricular sensing circuits 626, 670 and 628, 678 are able to trigger or inhibit the atrial and ventricular pulse generators 614 and 616. The switch 622 couples the pressure input terminal 658 with the data acquisition system 606. For example, the pressure sensing lead 154 (shown in FIG. 1) may be joined to the pressure input terminal 658, which then may be connected to the data acquisition system 606 via the switch 622. The switch 622 may then control when the data acquisition system 606 receives pressure signals from the pressure sensing lead 154.

The memory 608 may be embodied in a computer-readable storage medium such as a ROM, RAM, flash memory, or other type of memory. The microcontroller 600 is coupled to the memory 608 by a suitable data/address bus 634, wherein the programmable operating parameters and thresholds used by the microcontroller 600 are stored and modified, as required, in order to customize the operation of IMD 100 to suit the needs of a particular patient. The memory 608 may store data indicative of pressure measurements 316, long term base pressures 320, upper pressure thresholds 318, acceleration rates 402-418, deceleration rates 502-518, above-threshold counters, below-threshold counters, treatment confirmation thresholds, under-threshold confirmation references, initial pacing rates, target or peak pacing rates, initial pacing rates, and other data related to myocardial function, and the like, for a desired period of time (e.g., 6 hours, 12 hours, 18 hours or 24 hours, and the like). In one embodiment, the pressure measurements 316 may be communicated to the external device 610 for analysis in accordance with one or more of actions of the process 200.

The operating parameters of the IMD 100 may be non-invasively programmed into the memory 608 through a telemetry circuit 638 in communication with the external device 610, such as another external device, a trans-telephonic transceiver or a diagnostic system analyzer. The telemetry circuit 638 is activated by the microcontroller 600 by a control signal 640. The telemetry circuit 638 allows intra-cardiac electrograms, pressure measurements 316, upper pressure thresholds 318, long term base pressures 320, acceleration rates 402-418, deceleration rates 502-518, initial pacing rates, peak pacing rates, and status information relating to the operation of IMD 100 (as contained in the microcontroller 600 or memory 608), to be sent to the external device 610 through an established communication link 642. The IMD 100 additionally includes a battery 644, which provides operating power to all of the circuits shown within the housing 104, including the microcontroller 600. The IMD 100 also includes a physiologic sensor 646 that may be used to adjust pacing stimulation rate according to the exercise state of the patient.

In the case where IMD 100 is intended to operate as an ICD device, the IMD 100 detects the occurrence of a shift in one or more waveforms in detected cardiac signals that indicates an arrhythmia, and automatically applies an appropriate electrical shock therapy to the heart aimed at terminating the detected arrhythmia. To this end, the microcontroller 600 further controls a shocking circuit 648 by way of a control signal 650. The shocking circuit 648 generates shocking pulses of low (up to 0.5 joules), moderate (0.5-10 joules) or high energy (11 to 40 joules). Such shocking pulses are applied to the heart 102 (shown in FIG. 1) of the patient through at least two shocking electrodes, and as shown in this embodiment, selected from the housing 104, the left atrial coil electrode 128 (shown in FIG. 1), the RV coil electrode 134 (shown in FIG. 1), and/or the SVC coil electrode 138 (shown in FIG. 1). The IMD 100 includes an impedance measuring circuit 672 enabled by the microcontroller 600 via a control signal 674. The measuring circuit 672 may be electrically coupled to the switch 622 so that impedance at any desired electrode may be obtained.

Figure 8:
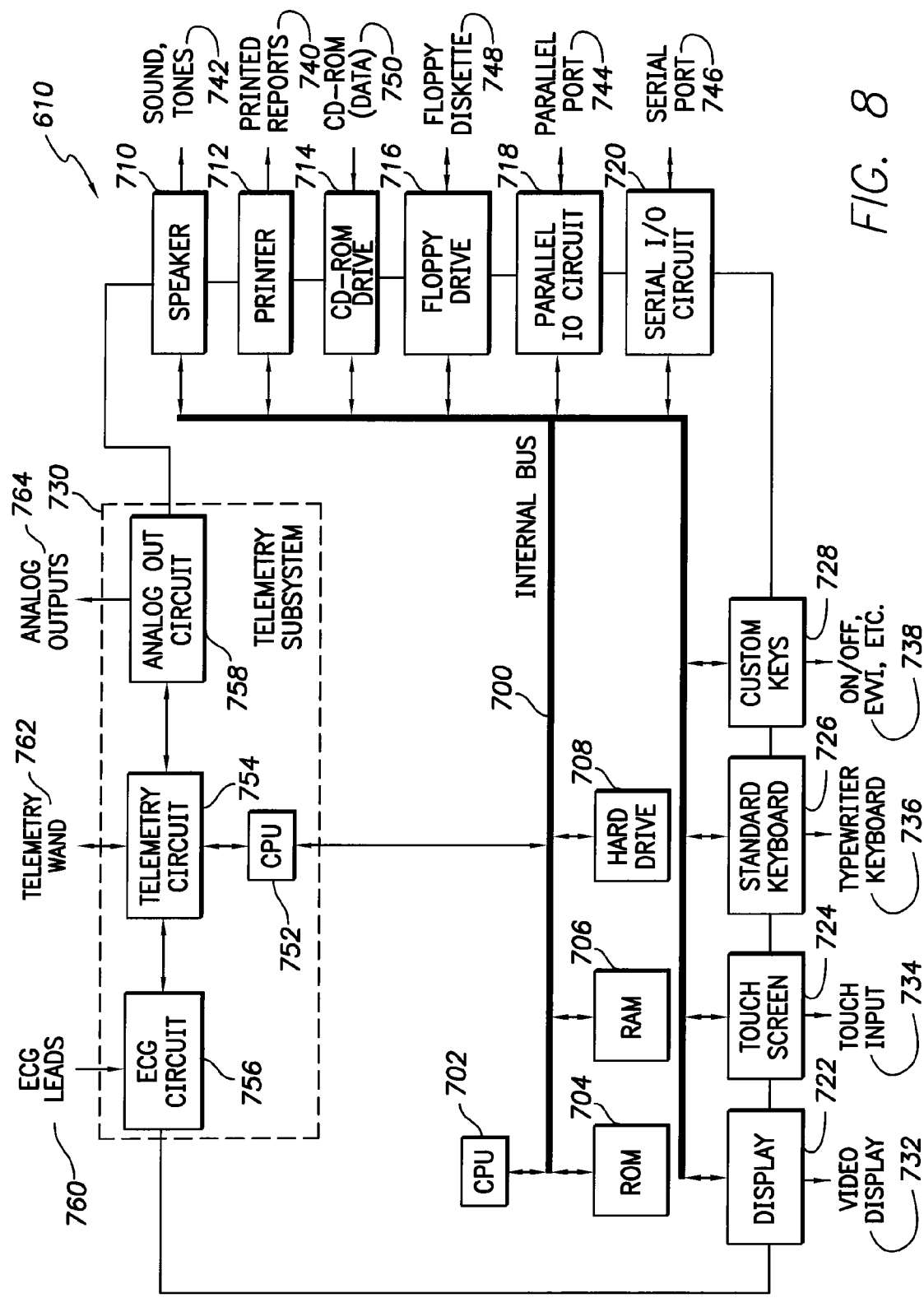
FIG. 8 illustrates a functional block diagram of an external device in accordance with one embodiment that is operated to interface with the IMD shown in FIG. 1.

FIG. 8 illustrates a functional block diagram of the external device 610, such as a programmer, that is operated by a physician, a health care worker, or a patient to interface with IMD 100. The external device 610 may be used by a physician or operator of the IMD 100 to set or adjust one or more of the long term base pressures 320 (shown in FIG. 4), upper pressure thresholds 318 (shown in FIG. 4), acceleration rates 402-418 (shown in FIG. 5), deceleration rates 502-518 (shown in FIG. 6), above-threshold counters, below-threshold counters, treatment confirmation thresholds, under-threshold confirmation references, target or peak pacing rates, and initial pacing rates.

The external device 610 may be utilized in a hospital setting, a physician's office, or even the patient's home to communicate with the IMD 100 to change a variety of operational parameters regarding the therapy provided by the IMD 100 as well as to select among physiological parameters to be monitored and recorded by the IMD 100. For example, the external device 610 may be used to program coronary episode related parameters, such as ischemia-related and acute myocardial infarction-related ST segment shift thresholds, duration thresholds, and the like. Further, the external device 610 may be utilized to interrogate the IMD 100 to determine the condition of a patient, to adjust the physiological parameters monitored or to adapt the therapy to a more efficacious one in a non-invasive manner. In one embodiment, the external device 610 is used to vary or set one or more of the long term base pressures 320 (shown in FIG. 4), upper pressure thresholds 318 (shown in FIG. 4), acceleration rates 402-418 (shown in FIG. 5), deceleration rates 502-518 (shown in FIG. 6), above-threshold counters, below-threshold counters, treatment confirmation thresholds, under-threshold confirmation references, peak rates, and initial pacing rates to prevent atrial overload and/or to reduce cardiac chamber pressure.

The external device 610 includes an internal bus 700 that connects/interfaces with a Central Processing Unit (CPU) 702, ROM 704, RAM 706, a hard drive 708, the speaker 710, a printer 712, a CD-ROM drive 714, a floppy drive 716, a parallel I/O circuit 718, a serial I/O circuit 720, the display 722, a touch screen 724, a standard keyboard connection 726, custom keys 728, and a telemetry subsystem 730. The internal bus 700 is an address/data bus that transfers information (e.g., either memory data or a memory address from which data will be either stored or retrieved) between the various components described herein. The hard drive 708 may store operational programs as well as data, such as the pressure measurements 316 (shown in FIG. 4), long term base pressures 320 (shown in FIG. 4), upper pressure thresholds 318 (shown in FIG. 4), acceleration rates 402-418 (shown in FIG. 5), deceleration rates 502-518 (shown in FIG. 6), above-threshold counters, below-threshold counters, treatment confirmation thresholds, under-threshold confirmation references, target or peak pacing rates, initial pacing rates, and the like.

The CPU 702 typically includes a microprocessor, a microcontroller, or equivalent control circuitry, designed specifically to control interfacing with the external device 610 and with the IMD 100. The CPU 702 may further include RAM or ROM memory, logic and timing circuitry, state machine circuitry, and I/O circuitry to interface with the IMD 100. Typically, the microcontroller 600 includes the ability to process or monitor input signals (e.g., data) as controlled by program code stored in memory (e.g., ROM 704).

The display 722 (e.g., may be connected to the video display 732) and the touch screen 724 display text, alphanumeric information, data and graphic information via a series of menu choices to be selected by the user relating to the IMD 100 (shown in FIG. 1), such as for example, status information, operating parameters, therapy parameters, patient status, access settings, software programming version, pressure measurements 316 (shown in FIG. 4), long term base pressures 320 (shown in FIG. 4), upper pressure thresholds 318 (shown in FIG. 4), acceleration rates 402-418 (shown in FIG. 5), deceleration rates 502-518 (shown in FIG. 6), above-threshold counters, below-threshold counters, treatment confirmation thresholds, under-threshold confirmation references, target or peak pacing rates, initial pacing rates, and the like. The touch screen 724 accepts a user's touch input 734 when selections are made. The keyboard 726 (e.g., a typewriter keyboard 736) allows the user to enter data to the displayed fields, operational parameters, therapy parameters, as well as interface with the telemetry subsystem 730. Furthermore, custom keys 728 turn on/off 738 (e.g., EVVI) the external device 610.

The printer 712 prints copies of reports 740 for a physician to review or to be placed in a patient file, and speaker 710 provides an audible warning (e.g., sounds and tones 742) to the user in the event of a potential deleterious programming value or if a patient has any abnormal physiological condition occur while the external device 610 is being used. The parallel I/O circuit 718 interfaces with a parallel port 744. The serial I/O circuit 720 interfaces with a serial port 746. The floppy drive 716 accepts diskettes 748. Optionally, the floppy drive 716 may include a USB port or other interface capable of communicating with a USB device such as a memory stick. The CD-ROM drive 714 accepts CD ROMs 750.

The telemetry subsystem 730 includes a central processing unit (CPU) 752 in electrical communication with a telemetry circuit 754, which communicates with both an ECG circuit 756 and an analog out circuit 758. The ECG circuit 756 is connected to ECG leads 760. The telemetry circuit 754 is connected to a telemetry wand 762. The analog out circuit 758 includes communication circuits, such as a transmitting antenna, modulation and demodulation stages (not shown), as well as transmitting and receiving stages (not shown) to communicate with analog outputs 764. The external device 610 may wirelessly communicate with the IMD 100 (shown in FIG. 1) and utilize protocols, such as Bluetooth, GSM, infrared wireless LANs, HIPERLAN, 3G, satellite, as well as circuit and packet data protocols, and the like. A wireless RF link utilizes a carrier signal that is selected to be safe for physiologic transmission through a human being and is below the frequencies associated with wireless radio frequency transmission. Alternatively, a hardwired connection may be used to connect the external device 610 to IMD 100 (e.g., an electrical cable having a USB connection).

Figure 9:
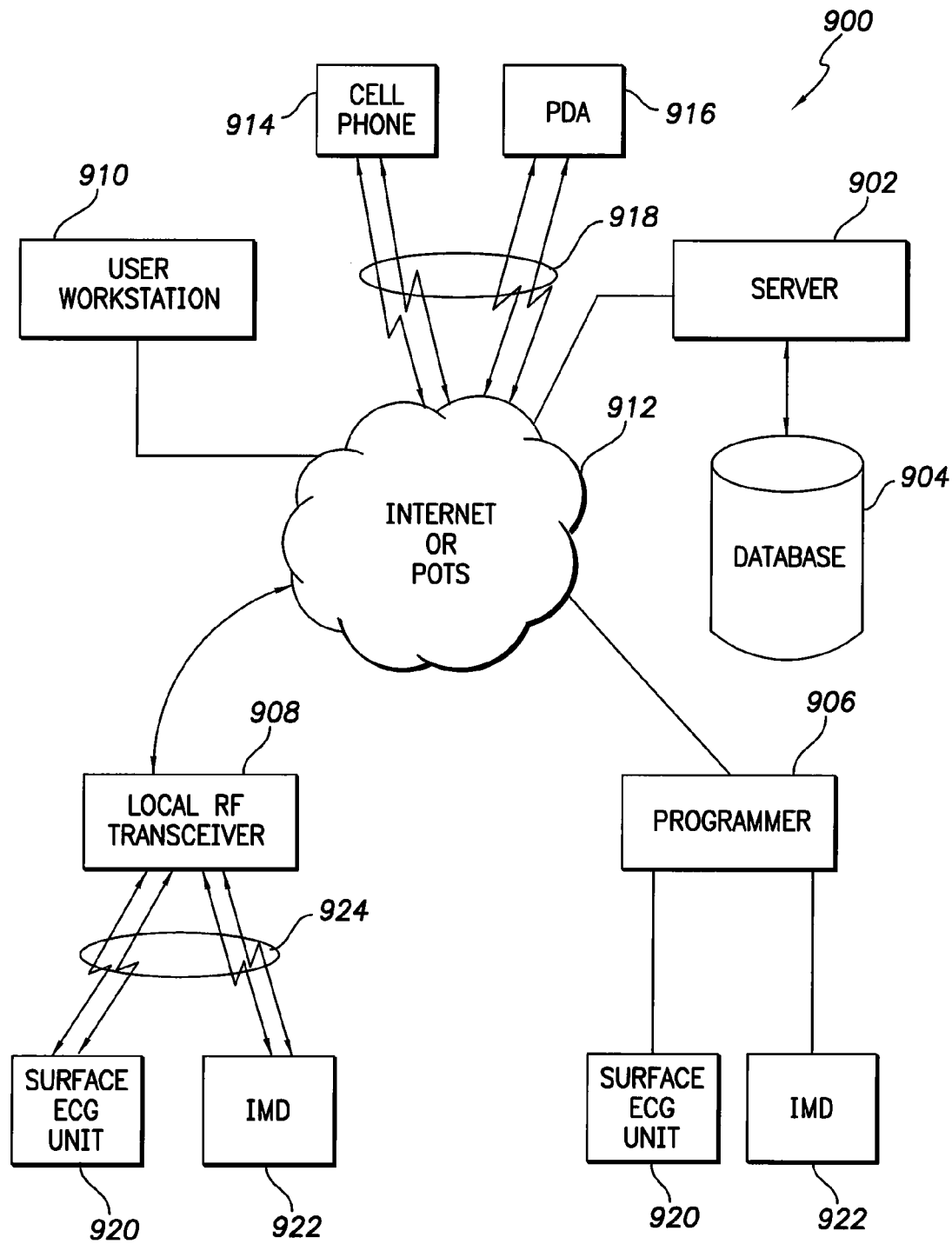
FIG. 9 illustrates a distributed processing system in accordance with one embodiment.

FIG. 9 illustrates a distributed processing system 900 in accordance with one embodiment. The distributed processing system 900 includes a server 902 that is connected to a database 904, a programmer 906 (e.g., similar to external device 610 described above and shown in FIG. 8), a local RF transceiver 908 and a user workstation 910 electrically connected to a communication system 912. The communication system 912 may be the internet, a voice over IP (VoIP) gateway, a local plain old telephone service (POTS) such as a public switched telephone network (PSTN), a cellular phone based network, and the like. Alternatively, the communication system 912 may be a local area network (LAN), a campus area network (CAN), a metropolitan area network (MAN), or a wide area network (WAM). The communication system 912 serves to provide a network that facilitates the transfer/receipt of cardiac signals, processed cardiac signals, histograms, trend analysis and patient status, and the like.

The server 902 is a computer system that provides services to other computing systems (e.g., clients) over a computer network. The server 902 acts to control the transmission and reception of information (e.g., cardiac signals, processed cardiac signals, pressure measurements 316 (shown in FIG. 4), long term base pressures 320 (shown in FIG. 4), upper pressure thresholds 318 (shown in FIG. 4), acceleration rates 402-418 (shown in FIG. 5), deceleration rates 502-518 (shown in FIG. 6), above-threshold counters, below-threshold counters, treatment confirmation thresholds, under-threshold confirmation references, target or peak pacing rates, initial pacing rates, and the like). The server 902 interfaces with the communication system 912 to transfer information between the programmer 906, the local RF transceiver 908, the user workstation 910 as well as a cell phone 914, and a personal data assistant (PDA) 916 to the database 904 for storage/retrieval of records of information. For instance, the server 902 may download, via a wireless connection 918, to the cell phone 914 or the PDA 916 the results of processed cardiac signals, the processes and analyses described above, pressure measurements 316 (shown in FIG. 4), long term base pressures 320 (shown in FIG. 4), upper pressure thresholds 318 (shown in FIG. 4), acceleration rates 402-418 (shown in FIG. 5), deceleration rates 502-518 (shown in FIG. 6), above-threshold counters, below-threshold counters, treatment confirmation thresholds, under-threshold confirmation references, target or peak pacing rates, initial pacing rates, or a patient's physiological state (e.g., is the patient is exhibiting instable myocardial behavior) based on previously recorded cardiac information. On the other hand, the server 902 may upload raw cardiac signals (e.g., unprocessed cardiac data) from a surface ECG unit 920 or an IMD 922 via the local RF transceiver 908 or the programmer 906. The IMD 922 may be similar to the IMD 100.

Database 904 is any commercially available database that stores information in a record format in electronic memory. The database 904 stores information such as raw cardiac data, processed cardiac signals, statistical calculations, histograms, cardiac trends (e.g., STS trends, trends in the reversal point percentages), cardiac chamber pressure data (e.g., pressure measurements 316 (shown in FIG. 4), long term base pressures 320 (shown in FIG. 4), upper pressure thresholds 318 (shown in FIG. 4), acceleration rates 402-418 (shown in FIG. 5), deceleration rates 502-518 (shown in FIG. 6), above-threshold counters, below-threshold counters, treatment confirmation thresholds, under-threshold confirmation references, target or peak pacing rates, and initial pacing rates) and the like. The information is downloaded into the database 904 via the server 902 or, alternatively, the information is uploaded to the server from the database 904.

The programmer 906 is similar to the external device 610 and may reside in a patient's home, a hospital, or a physician's office. Programmer 906 interfaces with the surface ECG unit 920 and the IMD 922. The programmer 906 may wirelessly communicate with the IMD 922 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 906 to IMD 922. The programmer 906 is able to acquire cardiac signals from the surface of a person (e.g., ECGs), intra-cardiac electrogram (e.g., IEGM) signals from the IMD 922, and/or pressure measurements 316 from the IMD 922. The programmer 906 interfaces with the communication system 912, either via the internet or via POTS, to upload the cardiac data acquired from the surface ECG unit 920 or the IMD 922 to the server 902. The programmer 906 may upload raw cardiac data, status information, operating parameters, therapy parameters, patient status, access settings, software programming version, cardiac chamber pressure data (e.g., pressure measurements 316, long term base pressures 320, upper pressure thresholds 318, acceleration rates 402-418, deceleration rates 502-518, above-threshold counters, below-threshold counters, treatment confirmation thresholds, under-threshold confirmation references, peak pacing rates, and initial pacing rates), and the like.

The local RF transceiver 908 interfaces with the communication system 912, via a communication link 924, to upload cardiac data acquired from the surface ECG unit 920 or the IMD 922 to the server 902. In one embodiment, the surface ECG unit 920 and the IMD 922 have a bidirectional connection with the local RF transceiver via a wireless connection. The local RF transceiver 908 is able to acquire cardiac signals from the surface of a person (e.g., ECGs), or acquire intra-cardiac electrogram (e.g., IEGM) signals from the IMD 922. On the other hand, the local RF transceiver 908 may download stored cardiac data from the database 904 or cardiac chamber pressure data (e.g., pressure measurements 316 (shown in FIG. 4), long term base pressures 320 (shown in FIG. 4), upper pressure thresholds 318 (shown in FIG. 4), acceleration rates 402-418 (shown in FIG. 5), deceleration rates 502-518 (shown in FIG. 6), above-threshold counters, below-threshold counters, treatment confirmation thresholds, under-threshold confirmation references, target or peak pacing rates, initial pacing rates, and the like) information to the surface ECG unit 920 or the IMD 922.

The user workstation 910 may interface with the communication system 912 via the internet or POTS to download information via the server 902 from the database 904. Alternatively, the user workstation 910 may download raw data from the surface ECG unit 920 or IMD 922 via either the programmer 906 or the local RF transceiver 908. Once the user workstation 910 has downloaded cardiac chamber pressure information (e.g., pressure measurements 316 (shown in FIG. 4), long term base pressures 320 (shown in FIG. 4), upper pressure thresholds 318 (shown in FIG. 4), acceleration rates 402-418 (shown in FIG. 5), deceleration rates 502-518 (shown in FIG. 6), above-threshold counters, below-threshold counters, treatment confirmation thresholds, under-threshold confirmation references, target or peak pacing rates, initial pacing rates, and the like), the user workstation 910 may process the information and adjust one or more of the long term base pressure 320, upper pressure threshold 318, acceleration rates 402-418, deceleration rates 502-518, above-threshold counters, below-threshold counters, treatment confirmation thresholds, under-threshold confirmation references, target or peak pacing rates, initial pacing rates, and the like. Once the user workstation 910 has finished performing its adjustments, the user workstation 910 may either download the results to the cell phone 916, the PDA 918, the local RF transceiver 908, the programmer 906, or to the server 902 to be stored on the database 904.

Figure 10:
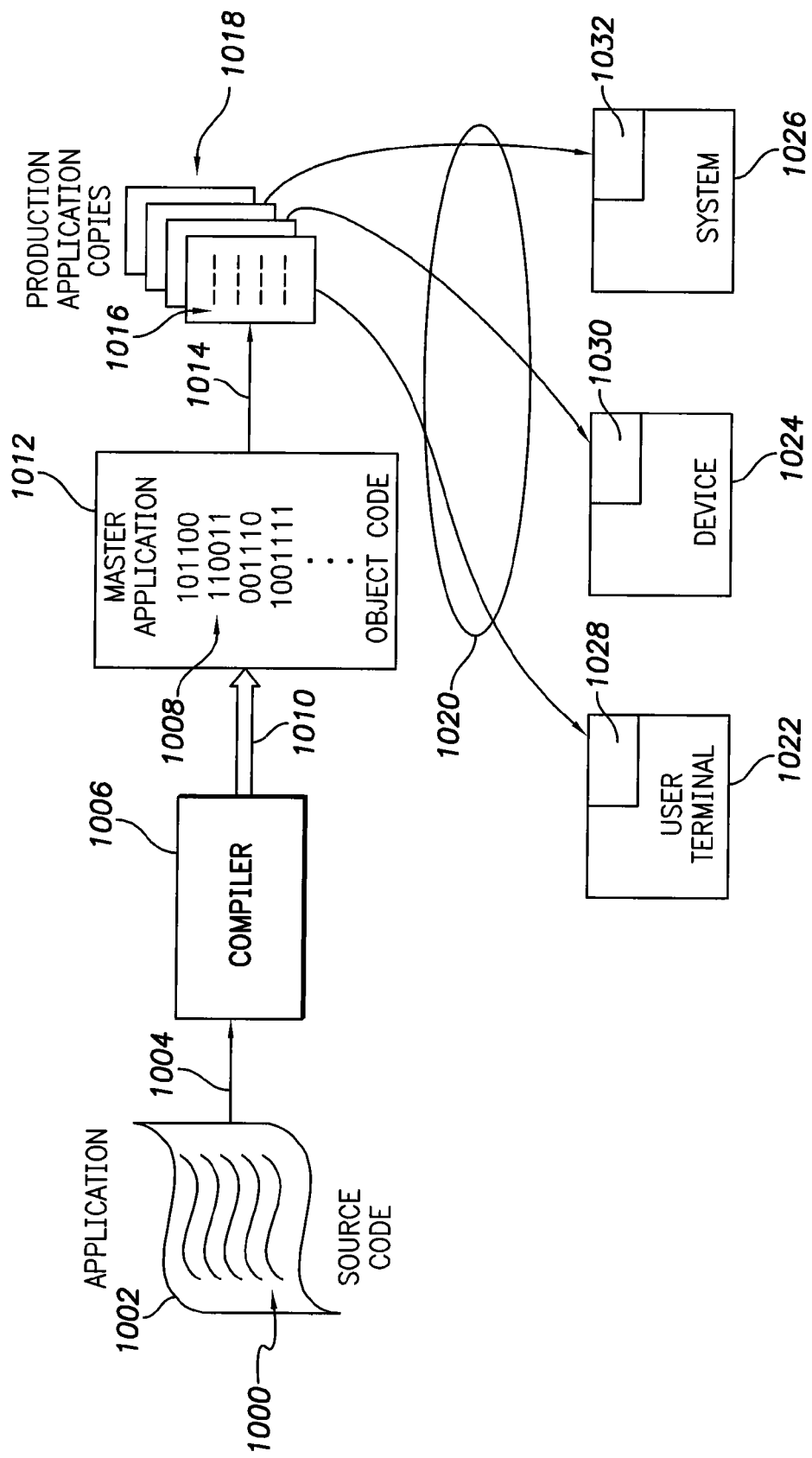
FIG. 10 illustrates a block diagram of manners in which embodiments of the present invention may be stored, distributed and installed on a computer-readable medium in accordance with one embodiment.

FIG. 10 illustrates a block diagram of exemplary manners in which embodiments of the present invention may be stored, distributed, and installed on a computer-readable medium. In FIG. 10, the "application" represents one or more of the methods and process operations discussed above. For example, the application may represent the processes carried out in connection with FIGS. 1 through 9 as discussed above. As shown in FIG. 10, the application is initially generated and stored as source code 1000 on a source computer-readable medium 1002. The source code 1000 is then conveyed over path 1004 and processed by a compiler 1006 to produce object code 1008. The object code 1008 is conveyed over path 1010 and saved as one or more application masters on a master computer-readable medium 1012. The object code 1008 is then copied numerous times, as denoted by path 1014, to produce production application copies 1016 that are saved on separate production computer-readable medium 1018. The production computer-readable medium 1018 is then conveyed, as denoted by path 1020, to various systems, devices, terminals and the like. In the example of FIG. 10, a user terminal 1022, a device 1024 and a system 1026 are shown as examples of hardware components, on which the production computer-readable medium 1018 are installed as applications (as denoted by 1028 through 1032). For example, the production computer-readable medium 1018 may be installed on the IMD 100 (shown in FIG. 1) and/or the microcontroller 600 (shown in FIG. 7).

The source code may be written as scripts, or in any high-level or low-level language. Examples of the source, master, and production computer-readable medium 1002, 1012, and 1018 include, but are not limited to, CDROM, RAM, ROM, Flash memory, RAID drives, memory on a computer system, and the like. Examples of the paths 1004, 1010, 1014, and 1020 include, but are not limited to, network paths, the internet, Bluetooth, GSM, infrared wireless LANs, HIPERLAN, 3G, satellite, and the like. The paths 1004, 1010, 1014, and 1020 may also represent public or private carrier services that transport one or more physical copies of the source, master, or production computer-readable medium 1002, 1012 or 1018 between two geographic locations. The paths 1004, 1010, 1014 and 1020 may represent threads carried out by one or more processors in parallel. For example, one computer may hold the source code 1000, compiler 1006 and object code 1008. Multiple computers may operate in parallel to produce the production application copies 1016. The paths 1004, 1010, 1014, and 1020 may be intra-state, inter-state, intra-country, inter-country, intra-continental, inter-continental, and the like.

The operations noted in FIG. 10 may be performed in a widely distributed manner world-wide with only a portion thereof being performed in the United States. For example, the application source code 1000 may be written in the United States and saved on a source computer-readable medium 1002 in the United States, but transported to another country (corresponding to path 1004) before compiling, copying and installation. Alternatively, the application source code 1000 may be written in or outside of the United States, compiled at a compiler 1006 located in the United States and saved on a master computer-readable medium 1012 in the United States, but the object code 1008 transported to another country (corresponding to path 1014) before copying and installation. Alternatively, the application source code 1000 and object code 1008 may be produced in or outside of the United States, but production application copies 1016 produced in or conveyed to the United States (for example, as part of a staging operation) before the production application copies 1016 are installed on user terminals 1022, devices 1024, and/or systems 1026 located in or outside the United States as applications 1028 through 1032.

As used throughout the specification and claims, the phrases "computer-readable medium" and "instructions configured to" shall refer to any one or all of (i) the source computer-readable medium 1002 and source code 1000, (ii) the master computer-readable medium and object code 1008, (iii) the production computer-readable medium 1018 and production application copies 1016 and/or (iv) the applications 1028 through 1032 saved in memory in the terminal 1022, device 1024, and system 1026.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A medical device comprising:
a pressure input configured to be joined to a pressure sensor located proximate to a cardiac chamber of a heart, the pressure input receiving pressure measurements representative of a pressure in the cardiac chamber;
an excitation source configured to deliver stimulation pulses to the heart at an initial pacing rate;
a detector module to communicate with the pressure sensor, the detector module receiving and comparing the pressure measurements to a pressure threshold; and
a processor adapted to instruct the excitation source to deliver the stimulation pulses at a pressure-based rate, higher than the initial pacing rate when the measured pressure exceeds the pressure threshold, the processor being further adapted to instruct the excitation source to cease delivery of the stimulation pulses at the pressure-based rate when the pressure measurements are no longer above the pressure threshold.

2. The device according to claim 1, further comprising a lead including the pressure sensor, the pressure sensor being configured to be located in at least one of a superior vena cava, a pulmonary artery, a pulmonary vein, the cardiac chamber, and a different cardiac chamber.

3. The device according to claim 1, wherein the processor instructs the excitation source to change the pressure-based rate from an initial pacing rate to a target rate.

4. The device according to claim 3, wherein the processor adjusts the pressure-based rate from the target rate to the initial pacing rate when the pressure measurements decrease below the pressure threshold.

5. The device according to claim 3, wherein the excitation source accelerates the pressure-based rate from the initial pacing rate to the target rate at a predetermined acceleration rate.

6. The device according to claim 5, further comprising a memory to store the predetermined acceleration rate, wherein the predetermined acceleration rate is programmable by an external device.

7. The device of claim 1, wherein, when the pressure measurements exceed the pressure threshold, the detector module continues to receive and compare the pressure measurements to the pressure threshold throughout a treatment confirmation window before the processor instructs the excitation source to adjust the pressure-based rate.

8. The device of claim 1, wherein, when the pressure measurements decrease below the pressure threshold and remain below the pressure threshold throughout an under-threshold continuity window, the processor then instructs the excitation source to cease delivery of the stimulation pulses at the pressure-based rate.

9. The device of claim 1, wherein, when the pressure measurements decrease below the pressure threshold for a predetermined minimum number of cardiac cycles, the processor instructs the excitation source to decrease a rate at which the excitation pulses are delivered downward from the pressure-based rate at a deceleration rate.

10. The device of claim 9, further comprising a memory to store the pressure threshold, wherein the pressure threshold is programmable by an external device.

11. A method for reducing a pressure in a cardiac chamber of a heart, the method comprising:
    delivering stimulation pulses to the heart at an initial pacing rate;
    obtaining pressure measurements representative of the pressure in the cardiac chamber;
    comparing the pressure measurements to a pressure threshold;
    delivering stimulation pulses to the heart at a pressure-based rate which is higher than the initial pacing rate when the measured pressure exceeds the pressure threshold; and
    ceasing delivery of the stimulation pulses at the pressure-based rate when the pressure measurements are no longer above the pressure threshold.

12. The method according to claim 11, wherein obtaining the pressure measurements comprises obtaining the pressure measurements in at least one of a superior vena cava, a pulmonary artery, a pulmonary vein, the cardiac chamber, and a different cardiac chamber.

13. The method according to claim 11, wherein delivering the stimulation pulses comprises changing the pressure-based rate from an initial pacing rate to a target rate.

14. The method according to claim 13, further comprising adjusting the pressure-based rate to the initial pacing rate when the pressure measurements decrease below the pressure threshold.

15. The method according to claim 13, further comprising accelerating the pressure-based rate from the initial pacing rate to the target rate at a predetermined acceleration rate.

16. The method of claim 11, wherein the pressure threshold represents at least one of an upper threshold and a long term base pressure.

17. A method for reducing a pressure in a cardiac chamber of a heart, the method comprising:
    obtaining pressure measurements representative of the pressure in the cardiac chamber;
    comparing the pressure measurements to a pressure threshold; and
    delivering stimulation pulses to the heart at a pressure-based rate based on the comparing of the pressure measurement to the pressure threshold, wherein obtaining the pressure measurements and comparing the pressure measurements comprise, after the pressure measurements exceed the pressure threshold, obtaining and comparing the pressure measurements to the pressure threshold throughout a treatment confirmation window before delivering the stimulation pulses at the pressure-based rate.

18. A method for reducing a pressure in a cardiac chamber of a heart, the method comprising:
    obtaining pressure measurements representative of the pressure in the cardiac chamber;
    comparing the pressure measurements to a pressure threshold; and
    delivering stimulation pulses to the heart at a pressure-based rate based on the comparing of the pressure measurement to the pressure threshold, wherein obtaining the pressure measurements and comparing the pressure measurements comprise, after the pressure measurements decrease below the pressure threshold and remain below the pressure threshold throughout an under-threshold continuity window, ceasing the delivering of the stimulation pulses at the pressure-based rate.

* * * * *